(12) United States Patent
Rosen et al.

(10) Patent No.: US 9,695,108 B2
(45) Date of Patent: Jul. 4, 2017

(54) COMPOUNDS AND METHODS OF USE THEREOF FOR TREATING TUMORS

(71) Applicant: Georgetown University, Washington, DC (US)

(72) Inventors: Eliot M. Rosen, Fairfax, VA (US); York A. Tomita, Bethesda, MD (US); Milton Brown, Brookeville, MD (US)

(73) Assignee: Georgetown University, Washington, DC (US)

(*) Notice: Subject to any disclaimer, the term of this patent is extended or adjusted under 35 U.S.C. 154(b) by 0 days.

(21) Appl. No.: 14/423,290

(22) PCT Filed: Aug. 23, 2013

(86) PCT No.: PCT/US2013/056501
§ 371 (c)(1),
(2) Date: Feb. 23, 2015

(87) PCT Pub. No.: WO2014/032019
PCT Pub. Date: Feb. 27, 2014

(65) Prior Publication Data
US 2015/0344440 A1  Dec. 3, 2015

Related U.S. Application Data

(60) Provisional application No. 61/692,419, filed on Aug. 23, 2012.

(51) Int. Cl.

| | |
|---|---|
| *C07C 69/92* | (2006.01) |
| *C07C 69/76* | (2006.01) |
| *C07C 53/136* | (2006.01) |
| *C07C 57/50* | (2006.01) |
| *C07C 311/42* | (2006.01) |
| *C07D 409/14* | (2006.01) |
| *C07D 257/04* | (2006.01) |
| *C07D 401/14* | (2006.01) |
| *C07D 307/33* | (2006.01) |
| *C07D 405/14* | (2006.01) |
| *C07D 487/18* | (2006.01) |
| *C07D 317/46* | (2006.01) |
| *C07D 317/58* | (2006.01) |
| *C07D 317/68* | (2006.01) |
| *C07D 239/42* | (2006.01) |
| *C07D 249/04* | (2006.01) |
| *C07C 57/40* | (2006.01) |
| *C07C 57/42* | (2006.01) |

(52) U.S. Cl.
CPC ............ *C07C 69/92* (2013.01); *C07C 53/136* (2013.01); *C07C 57/40* (2013.01); *C07C 57/42* (2013.01); *C07C 57/50* (2013.01); *C07C 69/76* (2013.01); *C07C 311/42* (2013.01); *C07D 239/42* (2013.01); *C07D 249/04* (2013.01); *C07D 257/04* (2013.01); *C07D 307/33* (2013.01); *C07D 317/46* (2013.01); *C07D 317/58* (2013.01); *C07D 317/68* (2013.01); *C07D 401/14* (2013.01); *C07D 405/14* (2013.01); *C07D 409/14* (2013.01); *C07D 487/18* (2013.01); *C07C 2101/02* (2013.01); *C07C 2103/24* (2013.01); *C07C 2103/26* (2013.01)

(58) Field of Classification Search
CPC ....... C07C 69/92; C07C 69/76; C07C 53/136; C07C 57/50; C07C 57/42; C07C 57/40; C07C 311/42; C07C 2103/26; C07C 2103/24; C07C 2103/02; C07D 409/14; C07D 257/04; C07D 401/14; C07D 307/33; C07D 405/14; C07D 317/46; C07D 317/58; C07D 317/68; C07D 239/42; C07D 487/18
See application file for complete search history.

(56) References Cited

U.S. PATENT DOCUMENTS

| | | |
|---|---|---|
| 2008/0227811 A1 | 9/2008 | Chen |
| 2010/0210727 A1 | 8/2010 | Pace-Asciak et al. |
| 2011/0053938 A1 | 3/2011 | Foley et al. |

OTHER PUBLICATIONS

J. Luo et al., 36 Cell, 823-837 (2009).*
T. Soussi 60 Cancer Research, 1777-1788 (2000).*
P. Lissoni et al, 7 Cancer Research, 397-401 (2009).*
National Cancer Institute (http://www.cancer.gov/) (Downloaded May 29, 2014).*
PCT/US2013/056501; International Search Report and Written Opinion dated Jan. 24, 2014.

* cited by examiner

*Primary Examiner* — Ebenezer O Sackey
(74) *Attorney, Agent, or Firm* — Morgan, Lewis & Bockius, LLP

(57) ABSTRACT

The invention encompasses novel compounds and pharmaceutically acceptable salts thereof and compositions including therapeutically or prophylactically effective amounts of such compounds or pharmaceutically acceptable salts thereof. The invention also encompasses methods for treating or preventing diseases and disorders associated with abnormal cell growth, for example, treating or preventing cancer or tumor growth, which methods include administering to a mammal in need thereof a composition comprising a therapeutically or prophylactically effective amount of a compound of the invention or a pharmaceutically acceptable salt thereof.

6 Claims, 2 Drawing Sheets

COMPOUNDS AND METHODS OF USE THEREOF FOR TREATING TUMORS

STATEMENT REGARDING FEDERALLY SPONSORED RESEARCH OR DEVELOPMENT

Part of the work performed during development of this invention utilized U.S. Government funds under National Institutes of Health (National Cancer Institute) Grant Nos. R01-CA82599 and R01-CA150646. The U.S. Government has certain rights in this invention.

BACKGROUND OF THE INVENTION

Field of the Invention

The invention encompasses novel compounds and pharmaceutically acceptable salts thereof and compositions including therapeutically or prophylactically effective amounts of such compounds or pharmaceutically acceptable salts thereof.

Background of the Invention

The BRCA1 gene was identified in 1994 based its linkage to hereditary breast and ovarian cancers. BRCA1 mutations also confer an increased risk for several other hormone-responsive tumor types (cervical, endometrial, and prostate cancers). BRCA1 is a protein with 1863 amino acids and is considered to be a nuclear phospho-protein with conserved N-terminal RING and C-terminal acidic transcriptional activation domains. A BRCA1 null mutation confers early embryonic lethality (day 7.5-8.5) in mice, due to a severe proliferation defect caused by p53 activation and consequent p21WAF1 expression, but a partial BRCA1 deletion targeted to the mammary gland allows survival with development of breast cancer. In mice, BRCA1 expression is widespread, but it is especially increased in rapidly proliferating cells in compartments that are also undergoing differentiation, including mammary epithelial cells during puberty and pregnancy.

Various functional activities are ascribed to BRCA1, but it is still unclear which of these are essential for cancer suppression. Early studies indicated that BRCA1 is expressed and phosphorylated cyclically, suggesting a role in cell cycle regulation. BRCA1 was found to interact with RB1 and to collaborate with RB1 in regulating progression from G1 to S phase. Most studies on BRCA1 function, however, have concentrated on its role in DNA repair. In response to DNA damage, BRCA1 is phosphorylated by several up-stream protein kinases (ATM (ataxia-telangiectasia mutated), ATR, and CHEK2) and associates with the RMN complex (Rad50-Mre11-p95NBS1) in radiation-induced nuclear "dots," suggesting a role in the repair of double-strand breaks. BRCA1 deficiency confers defects in several types of DNA repair mechanisms, including microhomology-dependent repair and homologous recombination. Studies of BRCA1 mutant cell types have also established roles for BRCA1 in several DNA damage-responsive cell cycle checkpoints (intra-S and G2/M). BRCA1 mutant cells exhibit evidence of genomic instability, e.g., centrosome amplification, aneuploidy, and chromosomal aberrations. In addition, BRCA1 is present in a large multi-protein BRCA1-associated genome surveillance complex (BASC). For these reasons, BRCA1 is thought to mediate a "caretaker" function in the maintenance of genomic stability.

Estrogen receptor-alpha (ER-α) is a member of the nuclear receptor superfamily of ligand activated transcription factors, characterized by: an N-terminal transactivation domain (AF-1), a conserved C-terminal activation domain (AF-2), which overlaps with the ligand binding domain (LBD), a sequence-specific DNA-binding domain (DBD), and a hinge region located between the DBD and AF-2 regions. BRCA1 is a strong inhibitor of E2-stimulated ER-α activity via a direct physical interaction with the AF-2 activation domain of ER-α. BRCA1 also represses ligand-independent activation of ER-α, since BRCA1-siRNA can stimulate ER-α activity in the absence of estrogen. This finding suggests that the endogenous levels of BRCA1 are sufficient to inhibit basal activity levels of ER-α. Further studies have documented that BRCA1 broadly inhibits E2-stimulated gene expression and blocks E2-stimulated proliferation of ER-α positive human breast cancer cells. BRCA1 has been detected at the ERE site of estrogen-regulated promoters (pS2 and cathepsin D), and exposure to E2 causes a rapid loss of BRCA1 from this site. Various breast cancer-associated BRCA1 mutations abrogate or greatly lessen the ability of BRCA1 to inhibit ER-α, suggesting that this function is essential for breast cancer suppression. Finally, it has recently been shown BRCA1 can inhibit the activity of aromatase (CYP19A1), a cytochrome P450 enzyme that mediates the conversion of androgens into estrogens, in epithelial cells and adipocytes.

About two-thirds of human sporadic (non-hereditary) breast cancers are ER-α positive, and hormonal factors clearly affect the risk for developing these tumors. In contrast to sporadic cancers, about two-thirds of BRCA1 mutant human breast cancers are ER-α negative. However, there is substantial evidence from clinical/epidemiologic studies and from experimental animal studies suggesting a hormonal etiology for BRCA1-mutant breast cancers, even though the tumors usually end up being ER-α negative.

For example, several studies provide evidence that BRCA1-mutant mammary carcinogenesis is estrogen-sensitive. For example, the chemoprevention agent Tamoxifen, which is a partial ER-α antagonist and agonist, can cause an increase in the prevalence of mammary hyperplasia and accelerated the development of mammary cancer in BRCA1$^{Co/Co}$/MMTV-Cre/p53$^{+/-}$ mice. These findings were consistent with the finding that in MCF-7 cells, BRCA1 knockdown shifted the balance of Tamoxifen activity from ER-α antagonist to agonist. Moreover, in BRCA1$^{Co/Co}$/MMTV-Cre/p53$^{+/-}$ mice, bilateral ovariectomy significantly reduced the incidence of mammary cancer. The ovariectomy was most effective in reducing cancer risk when performed well before the time the tumors normally occur. These results suggest that the early stages of BRCA1-dependent mammary tumorigenesis could be E2-dependent, and thus it may be possible to prevent or treat BRCA1-mutant breast cancers using an agent that can mimic the ability of BRCA1 to inhibit ER-α activity.

SUMMARY OF THE INVENTION

The invention relates to compounds, compositions and methods of use thereof of compounds of Formulas I-III.

In one embodiment, the invention is directed towards compounds of Formula I:

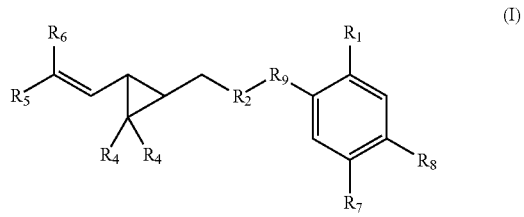

or pharmaceutically acceptable salts or prodrugs thereof, wherein
$R_1$, $R_3$, $R_4$, $R_5$, $R_6$, $R_7$ and $R_8$ are each independently H; a halogen; —OH; an amine; a carboxyl; substituted or unsubstituted: cyclic or acyclic alkyl group, cyclic or acyclic alkenyl group, cyclic or acyclic akynyl group, carboxyalkyl, cyclic or acyclic alkoxy, aryl group, alkylaryl group, arylalkyl group, heteroaryl group, heteroalkyl group; $COR_{10}$; $CSR_{10}$; $SOR_{10}$; $SO_2R_{10}$; $CON(R_{10})_2$; $CSN(R_{10})_2$; wherein $R_5$ and $R_6$, or $R_3$ and $R_4$, or $R_7$ and $R_8$ can form a 3-10 membered substituted or unsubstituted ring with one or more of C, S, O or N, $R_2$ is $CH_2$, $CHR_1$, $COR_1$, $CSR_1$, SO, $SO_2$, $SHOR_1$, NH, $NOR_1$ or O, $R_9$ is CO, O, NH or $CH_2$, and $R_{10}$ is H; —OH; an amine; a carboxyl; substituted or unsubstituted: cyclic or acyclic alkyl group, cyclic or acyclic alkenyl group, cyclic or acyclic akynyl group, an aryl group, an alkylaryl group, an arylalkyl group, heteroaryl group, heteroalkyl group; or a halogen.

In another embodiment, the invention is directed towards compounds of Formula II:

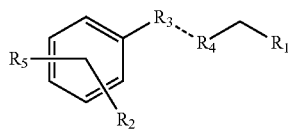

(II)

or pharmaceutically acceptable salts or prodrugs thereof, wherein $R_1$ is H; a halogen; —OH; an amine; a carboxyl; substituted or unsubstituted: cyclic or acyclic alkyl group, cyclic or acyclic alkenyl group, cyclic or acyclic akynyl group, carboxyalkyl, cyclic or acyclic alkoxy, aryl group, alkylaryl group, arylalkyl group, heteroaryl group, heteroalkyl group; $COR_8$; $CSR_8$; $SOR_8$; $SO_2R_8$; $CON(R_8)_2$; $CSN(R_8)_2$; wherein $R_1$ and $R_4$, can form a 3-10 membered ring with one or more of C, S, O or N;

$R_2$ and $R_5$ are each independently H; a halogen; —OH; an amine; a carboxyl; substituted or unsubstituted: cyclic or acyclic alkyl group, cyclic or acyclic alkenyl group, cyclic or acyclic alkynyl group, carboxyalkyl, cyclic or acyclic alkoxy, aryl group, alkylaryl group, arylalkyl group, heteroaryl group, heteroalkyl group; $COR_8$; $CSR_8$; $SOR_8$; $SO_2R_8$; $CON(R_8)_2$; $CSN(R_8)_2$; or a monocyclic or polycyclic substituted or unsubstituted fused ring structure that is fused with the ring atoms to which either $R_2$ or $R_5$ are attached; wherein $R_2$ and $R_5$ can form a 3-10 membered ring with one or more of C, S, O or N;

$R_3$ and $R_4$ are each independently CH; $C(R_1)_2$; CO; $COR_1$; $CON(R_1)_2$; CS; $CSR_1$; $CS(R_1)_2$; $C(SR_1)R_1$; $CSNR_1$; SH; SO; $SO_2$; $S(O)R_1$; $S(O)(R_1)_2$; N; NH; $NR_1$; $NOR_1$; or O; wherein $R_3$ and $R_4$, together with the ring atoms to which $R_4$ is attached, can form an additional fused 5- or 6-membered ring structure, with one or more of C, S, O or N; wherein $R_2$ and $R_3$ together with the ring atoms to which they are attached, can form an additional fused 5- or 6-membered ring structure, with one or more of C, S, O or N; wherein $R_3$ together with the ring atoms to which it is attached, can form an additional fused 5- or 6-membered ring structure, with one or more of C, S, O or N;

$R_8$ is H; —OH; an amine; a carboxyl; substituted or unsubstituted: cyclic or acyclic alkyl group, cyclic or acyclic alkenyl group, cyclic or acyclic akynyl group, an aryl group, an alkylaryl group, an arylalkyl group, heteroaryl group, heteroalkyl group; or a halogen; and ----- is a single bond or a double bond, wherein if ----- is a double bond, $R_3$ and $R_4$ are independently CH, N or SH.

In another embodiment, the invention is directed towards compounds of Formula III:

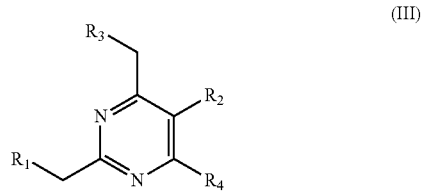

(III)

or pharmaceutically acceptable salts or prodrugs thereof, wherein $R_1$ and $R_3$ are each independently H; a halogen; —OH; an amine; a carboxyl; substituted or unsubstituted: cyclic or acyclic alkyl group, cyclic or acyclic alkenyl group, cyclic or acyclic akynyl group, carboxyalkyl, cyclic or acyclic alkoxy, aryl group, alkylaryl group, arylalkyl group, heteroaryl group, heteroalkyl group; $COR_8$; $CSR_8$; $SOR_8$; $SO_2R_8$; $CON(R_8)_2$; $CSN(R_8)_2$; wherein $R_1$ and $R_3$ can form a 6-15 membered ring with one or more of C, S, O or N, $R_2$ and $R_4$ are each independently H; a halogen; —OH; an amine; a carboxyl; substituted or unsubstituted: cyclic or acyclic alkyl group, cyclic or acyclic alkenyl group, cyclic or acyclic akynyl group, carboxyalkyl, cyclic or acyclic alkoxy, aryl group, alkylaryl group, arylalkyl group, heteroaryl group, heteroalkyl group; $COR_8$; $CSR_8$; $SOR_8$; $SO_2R_8$; $CON(R_8)_2$; $CSN(R_8)_2$; wherein $R_2$ and $R_4$ can form a monocyclic or polycyclic 3-14 membered fused ring structure, together with the atoms to which they are attached, with one or more of C, S, O or N, and $R_8$ is —H; —OH; an amine; a carboxyl; substituted or unsubstituted: cyclic or acyclic alkyl group, cyclic or acyclic alkenyl group, cyclic or acyclic akynyl group, an aryl group, an alkylaryl group, an arylalkyl group, heteroaryl group, heteroalkyl group; or a halogen.

DETAILED DESCRIPTION OF THE INVENTION

Figure 1:
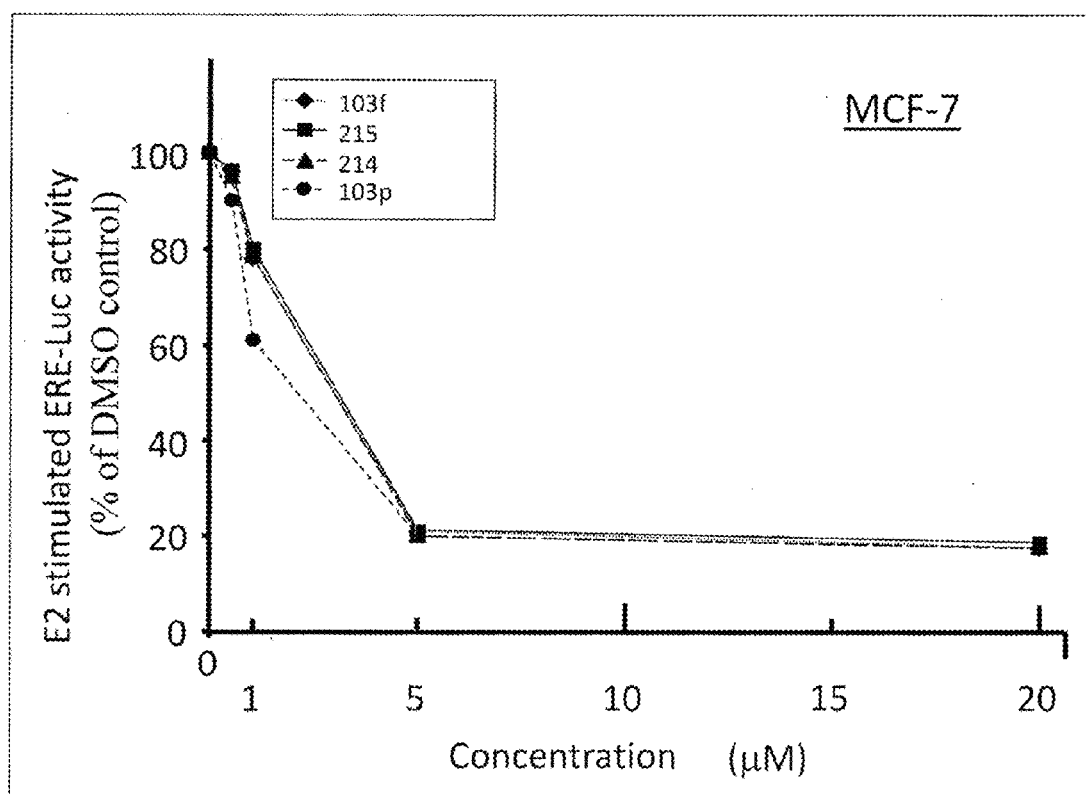
FIG. 1 depicts cellular activity of select compounds of the present invention with a luciferase reporter assay from an estrogen response element (ERE) in the MCF-7 human breast cancer cell line.
Figure 2:
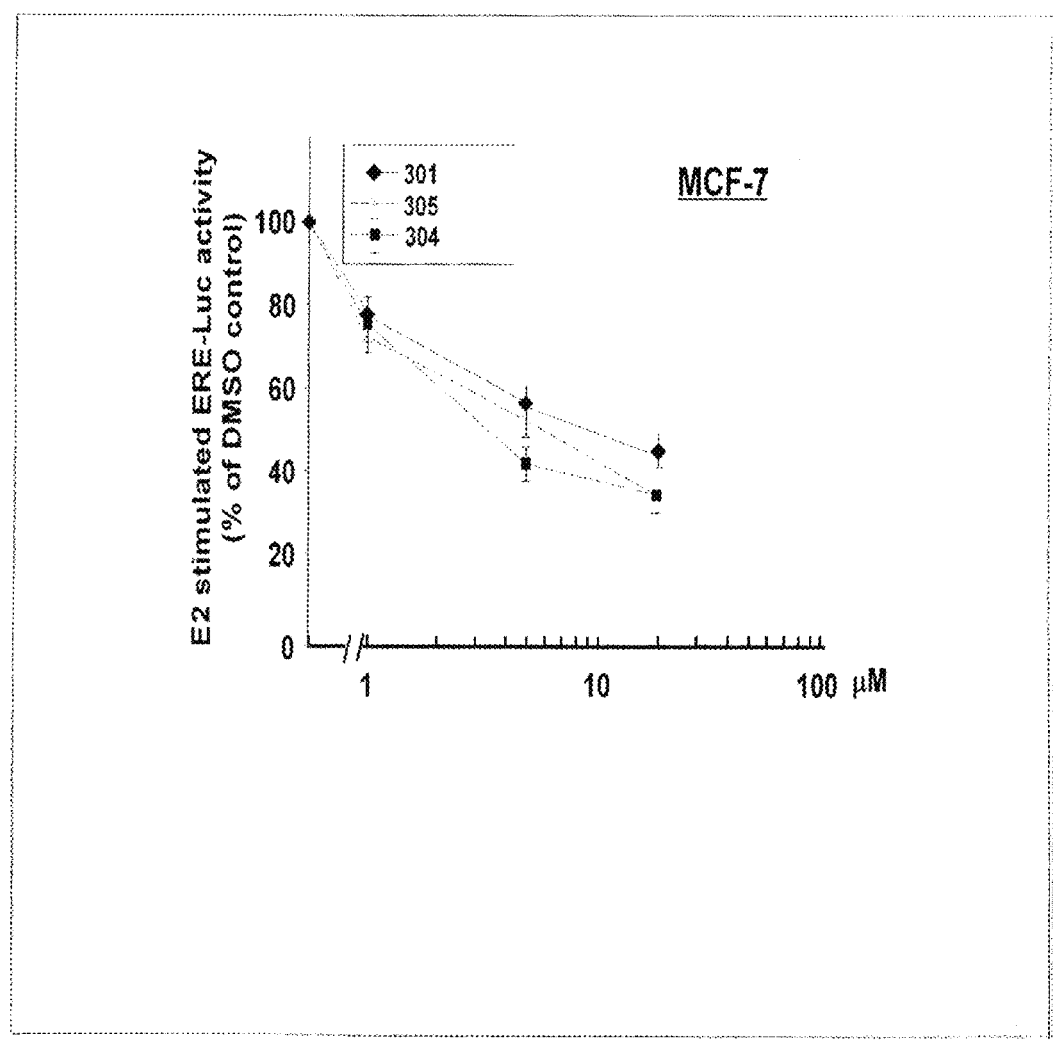
FIG. 2 depicts cellular activity of select compounds of the present invention with a luciferase reporter assay from an estrogen response element (ERE) in the MCF-7 human breast cancer cell line.

As used herein and unless otherwise indicated, the phrase "compound(s) of the invention" means, collectively, any of the compounds of Formulas I, II and III and pharmaceutically acceptable salts thereof. Examples of compounds of the present invention include but are not limited to the compounds depicted herein. The compounds of the invention are identified herein by their chemical structure and/or chemical name. Where a compound is referred to by both a chemical structure and a chemical name, and that chemical structure and chemical name conflict, the chemical structure is determinative of the compound's identity. The compounds of the invention may contain one or more chiral centers and/or double bonds and, therefore, exist as stereoisomers, such as double-bond isomers, i.e., geometric isomers, enantiomers, or diastereomers. According to the invention, the chemical structures depicted herein, and therefore the compounds of the invention, encompass all of the corresponding compounds' enantiomers and stereoisomers, i.e., both the stereomerically pure forms and enantiomeric and stereoisomeric mixtures. The term "stereomerically pure" is understood in the art and is used to mean geometrically pure, enantiomerically pure, or diastereomerically pure compounds. Enantiomeric and stereoisomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically- or enantiomerically-pure intermediates, reagents, and catalysts by well known asymmetric synthetic methods.

As used herein and unless otherwise indicated, the term "alkoxy group" means an —O-alkyl group, wherein alkyl is as defined herein. The alkoxy group can be cyclic or acyclic and can be unsubstituted or substituted with one or two suitable substituents. In one embodiment, the alkyl chain of an alkyloxy group is from 1 to 6 carbon atoms in length, referred to herein, for example, as "$(C_1-C_{10})$alkoxy."

As used herein, the term "substituted" and "a suitable substituent" when used in conjunction with a substituent of the compounds of the present invention, refers to a substituent, e.g., an alkyl or aryl, in which one or more hydrogen atom bound to any carbon or heteroatom is replaced by another group. The "substitutes" and the "suitable substituents" are groups that do not nullify the synthetic or pharmaceutical utility of the compounds of the invention or the intermediates useful for preparing them. Examples of substituted groups or suitable substituents include, but are not limited to: $(C_1-C_8)$alkyl; $(C_1-C_8)$alkenyl; $(C_1-C_8)$alkynyl; $(C_6)$aryl; $(C_3-C_5)$heteroaryl; $(C_3-C_7)$cycloalkyl; $(C_1-C_8)$alkoxy; $(C_6)$aryloxy; —CN; —OH; SH, oxo; halo, —NO$_2$, —CO$_2$H; —NH$_2$; —NHOH, —NH$((C_1-C_8)$alkyl); —N$((C_1-C_8)$alkyl)$_2$; —NH$((C_6)$aryl); —NHO$((C_1-C_8)$alkyl); —N$(O(C_1-C_8)$alkyl)$_2$; —NH$(O(C_6)$aryl); —S$((C_1-C_8)$alkyl); —S$((C_1-C_8)$alkyl)$_2$; —S$((C_6)$aryl); (=O); C(S), —N$((C_6)$aryl)$_2$; —CHO; —C(O)$((C_1-C_8)$alkyl); —C(O)$((C_6)$aryl); —CO$_2((C_1-C_8)$alkyl); and —CO$_2((C_6)$aryl), —C(S)$((C_1-C_8)$alkyl); —C(S)$((C_6)$aryl); —SO$_2((C_1-C_8)$alkyl); —SO$_2((C_6)$aryl), and —SO$_3$H, —C(S)O$((C_1-C_8)$alkyl); —C(S)(O)$((C_6)$aryl). In additional illustrative embodiments, the substituents can be one or more than one suitable groups, such as, but not limited to, —F, —Cl, —Br, —I, —OH, azido, —SH, alkyl, aryl, substituted aryl, cycloalkyl, substituted cycloalkyl, heterocycloalkyl, substituted heterocycloalkyl, heteroalkyl, alkyoxyl, alkylhalos, e.g., CF$_3$, alkylthiol, amino, phosphido, hydroxylamino, N-alkylamino, —N,N-dialkylamino, —N,N-dimethylamino, acyl, alkyloxycarbonyl, sulfonyl, urea, —NO$_2$, triazolyl, thio, and combinations thereof. One of skill in art can readily choose a suitable substituent based on the stability and pharmacological and synthetic activity of the compound of the invention.

As used herein and unless otherwise indicated, the term "alkenyl group" means a monovalent unbranched or branched hydrocarbon chain having one or more double bonds therein. The double bond of an alkenyl group can be unconjugated or conjugated to another unsaturated group. Suitable alkenyl groups include, but are not limited to (C$_2$-C$_8$)alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. The alkenyl group can be cyclic or acyclic and can be unsubstituted or substituted with one or two suitable substituents.

As used herein and unless otherwise indicated, the term "heteroalkenyl" is an alkenyl group as defined herein having at least one heteroatom incorporated within the alkenyl group. In certain embodiments, one of the hydrogen atoms can be substituted with a group having a heteroatom. For example, the group can be a hydroxyl group (OH) or thiol group (SH). Other examples of groups containing one or more heteroatoms include but are not limited to, nitro, amino, ester, carboxylic acid, carbamide, sulfonate, sulfonic acid, alkoxy, or SO$_2$R or S(O)$_2$OR, where R can be hydrogen or an alkyl group described above. Alternatively, one of the carbon atoms of the alkyl group can be substituted with a heteroatom. Examples of heteroatoms include, but are not limited to, nitrogen, oxygen, sulfur, and phosphorous. The heteroalkenyl group can be cyclic or acyclic and can be substituted or unsubstituted.

As used herein and unless otherwise indicated, the term "alkylalkoxy" or "alkyloxyalkyl group" means a saturated, monovalent unbranched or branched hydrocarbon chain covalently bonded to an oxygen and covalently bonded to a second a saturated, monovalent unbranched or branched hydrocarbon chain (e.g., -alkyl-O-alkyl). The alkyloxy group can be cyclic or acyclic and can be substituted or unsubstituted.

As used herein and unless otherwise indicated, the term "alkyl" or "alkyl group" means a substituted or unsubstituted, saturated, monovalent unbranched or branched hydrocarbon chain.

Examples of alkyl groups include, but are not limited to, $(C_1-C_{10})$alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl, and longer alkyl groups, such as heptyl, and octyl. An alkyl group can be unsubstituted or substituted with one or two suitable substituents.

As used herein and unless otherwise indicated, the term "heteroalkyl" is an alkyl group as defined herein having at least one heteroatom incorporated within the alkyl group. In certain embodiments, one of the hydrogen atoms can be substituted with a group having a heteroatom. For example, the group can be a hydroxyl group (OH) or thiol group (SH). Other examples of groups containing one or more heteroatoms include but are not limited to, nitro, amino, ester, carboxylic acid, carbamide, sulfonate, sulfonic acid, alkoxy, or SO$_2$R or S(O)$_2$OR, where R can be hydrogen or an alkyl group described above. Alternatively, one of the carbon atoms of the alkyl group can be substituted with a heteroatom. Examples of heteroatoms include, but are not limited to, nitrogen, oxygen, sulfur, and phosphorous. The heteroalkyl group can be cyclic or acyclic and can be substituted or unsubstituted.

As used herein and unless otherwise indicated, the term "alkynyl group" means monovalent unbranched or branched hydrocarbon chain having one or more triple bonds therein. The triple bond of an alkynyl group can be unconjugated or conjugated to another unsaturated group. Suitable alkynyl groups include, but are not limited to, (C$_2$-C$_6$)alkynyl groups, such as ethynyl, propynyl, butynyl, pentynyl, hexynyl, methylpropynyl, 4-methyl-1-butynyl, 4-propyl-2-pentynyl, and 4-butyl-2-hexynyl. An alkynyl group can be unsubstituted or substituted with one or two suitable substituents.

As used herein and unless otherwise indicated, the term "heteroalkynyl" is an alkynyl group as defined herein having at least one heteroatom incorporated within the alkynyl group. In certain embodiments, one of the hydrogen atoms can be substituted with a group having a heteroatom. For example, the group can be a hydroxyl group (OH) or thiol group (SH). Other examples of groups containing one or more heteroatoms include but are not limited to, nitro, amino, ester, carboxylic acid, carbamide, sulfonate, sulfonic acid, alkoxy, or $SO_2R$ or $S(O)_2OR$, where R can be hydrogen or an alkyl group described above. Alternatively, one of the carbon atoms of the alkyl group can be substituted with a heteroatom. Examples of heteroatoms include, but are not limited to, nitrogen, oxygen, sulfur, and phosphorous. The heteroalkynyl group can be cyclic or acyclic and can be substituted or unsubstituted.

As used herein and unless otherwise indicated, the term "amine" can include a primary, a secondary and/or a tertiary amine group.

As used herein and unless otherwise indicated, the term "aryl group" means a monocyclic or polycyclic-aromatic radical comprising carbon and hydrogen atoms. Examples of suitable aryl groups include, but are not limited to, phenyl, tolyl, anthacenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or two suitable substituents. In one embodiment, the aryl group is a monocyclic ring, wherein the ring comprises 6 carbon atoms, referred to herein as "$(C_6)$aryl."

As used herein and unless otherwise indicated, the term "phenyl" means —$C_6H_5$. A phenyl group can be unsubstituted or substituted with one or two suitable substituents.

As used herein and unless otherwise indicated, the term "heteroaryl group" means a monocyclic- or polycyclic aromatic ring comprising carbon atoms, hydrogen atoms, and one or more heteroatoms, for example 1 to 3 heteroatoms, independently selected from nitrogen, oxygen, and sulfur. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, furyl, thienyl, isoxazolyl, thiazolyl, furyl, phenyl, isoxazolyl, and oxazolyl. A heteroaryl group can be unsubstituted or substituted with one or two suitable substituents. In one embodiment, a heteroaryl group is a monocyclic ring, wherein the ring comprises 2 to 5 carbon atoms and 1 to 3 heteroatoms, referred to herein as "$(C_2-C_5)$heteroaryl."

As used herein, the term "benzyl" means —$CH_2$-phenyl.

As used herein and unless otherwise indicated, the term "aryloxy group" means an —O-aryl group, wherein aryl is as defined herein. An aryloxy group can be unsubstituted or substituted with one or two suitable substituents. In one embodiment, the aryl ring of an aryloxy group is a monocyclic ring, wherein the ring comprises 6 carbon atoms, referred to herein as "$(C_6)$aryloxy."

As used herein, the term "carbonyl" group is a divalent group of the formula —C(O)—.

As used herein and unless otherwise indicated, the term "carboxyalkyl" means an alkyl group as defined herein that has been substituted with at least one carboxy group.

As used herein and unless otherwise indicated, the terms "cyclic alkyl" and "cycloalkyl group" are used interchangeably and mean a monocyclic or polycyclic saturated ring comprising carbon and hydrogen atoms and having no carbon-carbon multiple bonds. Examples of cycloalkyl groups include, but are not limited to, $(C_3-C_7)$cycloalkyl groups, such as cyclopropyl, cyclobutyl, cyclopentyl, cyclohexyl, and cycloheptyl, and saturated cyclic and bicyclic terpenes. A cycloalkyl group can be unsubstituted or substituted by one or two suitable substituents. In one embodiment, the cycloalkyl group is a monocyclic ring or bicyclic ring.

As used herein and unless otherwise indicated, the term "heterocycloalkyl group" means a monocyclic or polycyclic ring comprising carbon and hydrogen atoms and at least one heteroatom, for example, 1 to 3 heteroatoms selected from nitrogen, oxygen, and sulfur, and having no unsaturation. Examples of heterocycloalkyl groups include but are not limited to pyrrolidinyl, pyrrolidino, piperidinyl, piperidino, piperazinyl, piperazino, morpholinyl, morpholino, thiomorpholinyl, thiomorpholino, and pyranyl. A heterocycloalkyl group can be unsubstituted or substituted with one or two suitable substituents. In one embodiment, the heterocycloalkyl group is a monocyclic or bicyclic ring. In a more specific embodiment, the heterocycloalkyl group is a monocyclic ring, wherein the ring comprises from 3 to 7 carbon atoms and from 1 to 3 heteroatoms, referred to herein as "$(C_1-C_7)$heterocycloalkyl."

As used herein and unless otherwise indicated, the terms "cyclic alkenyl" and "cycloalkenyl group" are used interchangeably and mean a monocyclic or polycyclic, unsaturated, non-aromatic ring comprising carbon and hydrogen atoms. Examples of cycloalkenyl groups include, but are not limited to, $(C_3-C_{10})$cycloalkenyl groups, such as cyclopropenyl, cyclobutenyl, cyclopentenyl, cyclohexenyl, cycloheptenyl, and cyclooctenyl, and unsaturated cyclic and bicyclic terpenes. A cycloalkenyl group can be unsubstituted or substituted by one or two suitable substituents. In one embodiment, the cycloalkenyl group is a monocyclic ring or bicyclic ring.

As used herein and unless otherwise indicated, the term "heterocycloalkenyl group" means a cycloalkenyl group as defined above, but with at least one heteroatom, for example, 1 to 3 heteroatoms selected from nitrogen, oxygen, and sulfur. A heterocycloalkenyl group can be unsubstituted or substituted with one or two suitable substituents. In one embodiment, the heterocycloalkenyl group is a monocyclic or bicyclic ring. In a more specific embodiment, the heterocycloalkenyl group is a monocyclic ring, wherein the ring comprises from 3 to 8 carbon atoms and from 1 to 3 heteroatoms, referred to herein as "$(C_3-C_8)$heterocycloalkyl."

As used herein and unless otherwise indicated, the terms "cyclic alkynyl" and "cycloalkynyl group" are used interchangeably and mean a monocyclic or polycyclic unsaturated ring comprising carbon and hydrogen atoms and having at least carbon-carbon triple bond. A cycloalkynyl group can be unsubstituted or substituted by one or two suitable substituents. In one embodiment, the cycloalkynyl group is a monocyclic ring or bicyclic ring.

As used herein and unless otherwise indicated, the term "heterocycloalkynyl group" means a cycloalkynyl group as defined above, but with at least one heteroatom, for example, 1 to 3 heteroatoms selected from nitrogen, oxygen, and sulfur. A heterocycloalkenyl group can be unsubstituted or substituted with one or two suitable substituents. In one embodiment, the heterocycloalkenyl group is a monocyclic or bicyclic ring. In a more specific embodiment, the heterocycloalkenyl group is a monocyclic ring, wherein the ring comprises from 8 to 12 carbon atoms and from 1 to 3 heteroatoms, referred to herein as "$(C_8-C_{12})$heterocycloalkynyl."

As used herein and unless otherwise indicated, the term "heterocyclic radical" or "heterocyclic ring" means a heterocycloalkyl group or a heteroaryl group.

As used herein and unless otherwise indicated, the term "halogen" means fluorine, chlorine, bromine, or iodine. Correspondingly, the meaning of the terms "halo" and "Hal" encompass fluoro, chloro, bromo, and iodo.

As used herein and unless otherwise indicated, the term "formulation" refers to a composition comprising a compound of the invention that is described in a particular dosage form (e.g., tablet) or with a particular dosage amount (e.g., 30 mg/kg).

As used herein and unless otherwise indicated, the term "hydrocarbyl group" means a monovalent group selected from $(C_1-C_8)$alkyl, $(C_2-C_8)$alkenyl, and $(C_2-C_8)$alkynyl, optionally substituted with one or two suitable substituents. In one embodiment, the hydrocarbon chain of a hydrocarbyl group is from 1 to 6 carbon atoms in length, referred to herein as "$(C_1-C_6)$hydrocarbyl."

When administered to a mammal (e.g., to an animal for veterinary use or to a human for clinical use), the compounds of the invention can be optionally administered in isolated form. As used herein, "isolated" means that the compounds of the invention are at least partially removed from its natural or original environment, for example (a) a natural source, such as a plant or cell culture or (b) a synthetic organic chemical reaction mixture in which the compound is initially produced. For example, an isolated compound of the present invention as used herein may still have residual components from the original chemical reaction and not necessarily purified to any level. As used herein, "purified" means that when isolated, the isolate contains at least 80%, 85%, 90%, 95%, 96%, 97%, 98% and 99% of the compound of the invention by weight.

The phrase "pharmaceutically acceptable salt(s)," as used herein includes but is not limited to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions including, but not limited to, sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions that are acidic in nature are capable of forming base salts with various pharmacologically acceptable cations. Examples of such salts include alkali metal or alkaline earth metal salts and, particularly, calcium, magnesium, sodium lithium, zinc, potassium, and iron salts.

As used herein and unless otherwise indicated, the term "pharmaceutically acceptable prodrug" means a derivative of a compound that can hydrolyze, oxidize, or otherwise react under biological conditions, in vitro or in vivo, to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include but are not limited to compounds that comprise oligonucleotides, peptides, lipids, aliphatic and aromatic groups, or NO, $NO_2$, ONO, and $ONO_2$ moieties. Prodrugs can typically be prepared using well known methods, such as those described in Burger's Medicinal Chemistry and Drug Discovery, pp. 172, 178, 949, 982 (Manfred E. Wolff ed., 5th ed. 1995), and Design of Prodrugs (H. Bundgaard ed., Elsevier, New York 1985).

As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, lower acyloxyalkyl esters (such as acetoxylmethyl, acetoxyethyl, aminocarbonyloxy-methyl, pivaloyloxymethyl, and pivaloyloxyethyl esters), lactonyl esters (such as phthalidyl and thiophthalidyl esters), lower alkoxyacyloxyalkyl esters (such as methoxycarbonyloxy-methyl, ethoxycarbonyloxyethyl and isopropoxycarbonyloxyethyl esters), alkoxyalkyl esters, choline esters, and acylamino alkyl esters (such as acetamidomethyl esters). Examples of biohydrolyzable amides include, but are not limited to, lower alkyl amides, a amino acid amides, alkoxyacyl amides, and alkylaminoalkyl-carbonyl amides. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein and unless otherwise indicated, the phrase "therapeutically effective amount" of a composition of the invention is measured by the therapeutic effectiveness of a compound of the invention, wherein at least one adverse effect of a disorder is ameliorated or alleviated.

As set forth herein, the invention includes, but is not limited to, compounds, compositions and formulations for treating or preventing treating or preventing a disease or disorder including, but not limited to, conditions caused by uncontrolled cell growth, hyperproliferation of cells, tumor growth, and cancers, for example, lung cancer, pancreatic cancer, leukemia, breast cancer, liver cancer, kidney cancer, ovarian cancer, human glioblastoma and prostate cancer, which comprises administering to a mammal in need of such treatment or prevention a therapeutically or prophylactically effective amount of a composition comprising a compound of Formula I, II or III, or a pharmaceutically acceptable salt or prodrug thereof, and a pharmaceutically acceptable vehicle. In certain embodiments, a composition or formulation comprising a compound of Formula I, II or III is useful in treating or preventing conditions caused by uncontrolled cell growth. In certain embodiments, a composition or formulation comprising a compound of Formula I, II or III is useful in killing abnormal or cancerous cells while simultaneously not affecting healthy or normal cells. In certain embodiments, a composition or formulation comprising a compound of Formula I, II or III act as cytotoxic agents. In certain embodiments, a composition or formulation comprising a compound of Formula I, II or III act as apoptotic agents. The compounds and compositions of Formulas I, II or III can be used in ER-α-positive cells and ER-α-negative cells. In addition, the compounds and compositions of Formulas I, II or III can be used in cells with a BRCA1 mutation and in cells without a BRCA1 mutation.

In one embodiment, the present invention encompasses compounds and compositions and formulations for treating abnormal cell growth comprising contacting the cell or cells with at least one compound of Formula I:

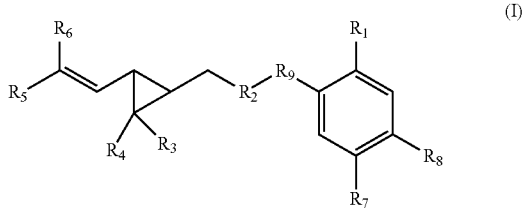

or pharmaceutically acceptable salts or prodrugs thereof, wherein $R_1$, $R_3$, $R_4$, $R_5$, $R_6$, $R_7$ and $R_8$ are each independently H; a halogen; —OH; an amine; a carboxyl; substituted or unsubstituted: cyclic or acyclic alkyl group, cyclic or acyclic alkenyl group, cyclic or acyclic akynyl group, carboxyalkyl, cyclic or acyclic alkoxy, aryl group, alkylaryl group, arylalkyl group, heteroaryl group, heteroalkyl group; $COR_{10}$; $CSR_{10}$; $SOR_{10}$; $SO_2R_{10}$; $CON(R_{10})_2$; $CSN(R_{10})_2$; wherein $R_5$ and $R_6$, or $R_3$ and $R_4$, or $R_7$ and $R_8$ can form a 3-10 membered substituted or unsubstituted ring with one or more of C, S, O or N, $R_2$ is $CH_2$, $CHR_1$, $COR_1$, $CSR_1$, SO, $SO_2$, $SHOR_1$, NH, $NOR_1$ or O, $R_9$ is CO, O, NH or $CH_2$, and $R_{10}$ is H; —OH; an amine; a carboxyl; substituted or unsubstituted: cyclic or acyclic alkyl group, cyclic or acyclic alkenyl group, cyclic or acyclic akynyl group, an aryl group, an alkylaryl group, an arylalkyl group, heteroaryl group, heteroalkyl group; or a halogen.

In one specific embodiment, the present invention encompasses compounds and compositions and formulations for treating abnormal cell growth comprising contacting the cell or cells with at least one compound of Formula Ia below. Formula I herein includes but is not limited to all embodiments that are represented by Formula Ia below:

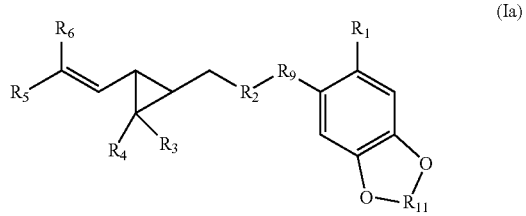

or pharmaceutically acceptable salts or prodrugs thereof, wherein $R_1$, $R_3$, $R_4$, $R_5$ and $R_6$, are each independently H; a halogen; —OH; an amine; a carboxyl; substituted or unsubstituted: cyclic or acyclic alkyl group, cyclic or acyclic alkenyl group, cyclic or acyclic akynyl group, carboxyalkyl, cyclic or acyclic alkoxy, aryl group, alkylaryl group, arylalkyl group, heteroaryl group, heteroalkyl group; $COR_{10}$; $CSR_{10}$; $SOR_{10}$; $SO_2R_{10}$; $CON(R_{10})_2$; $CSN(R_{10})_2$; wherein $R_5$ and $R_6$, or $R_3$ and $R_4$ can form a 3-10 membered substituted or unsubstituted ring with one or more of C, S, O or N, $R_2$ is $CH_2$, $CHR_1$, $COR_1$, $CSR_1$, SO, $SO_2$, $SHOR_1$, NH, $NOR_1$ or O, $R_9$ is CO, O, NH or $CH_2$, and $R_{10}$ is H; —OH; an amine; a carboxyl; substituted or unsubstituted: cyclic or acyclic alkyl group, cyclic or acyclic alkenyl group, cyclic or acyclic akynyl group, an aryl group, an alkylaryl group, an arylalkyl group, heteroaryl group, heteroalkyl group; or a halogen, and $R_{11}$ is $CH_2$, $CHR_1$ or $NR_1$.

Illustrative specific embodiments of compounds of the present invention useful in the methods for treating abnormal cell growth include but are not limited to compounds 101-114 disclosed below.

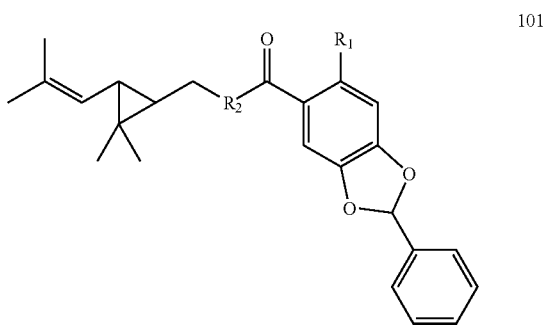

101

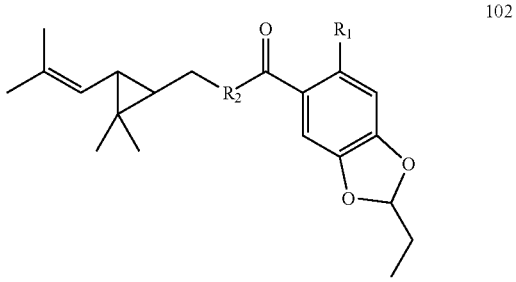

102

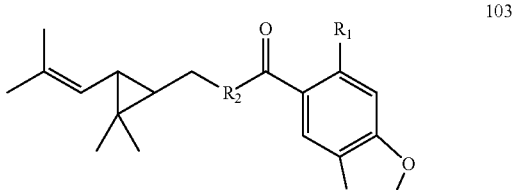

103

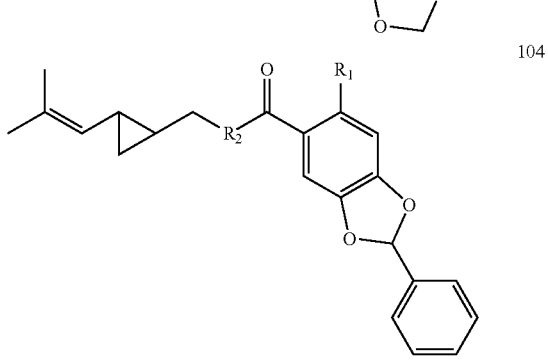

104

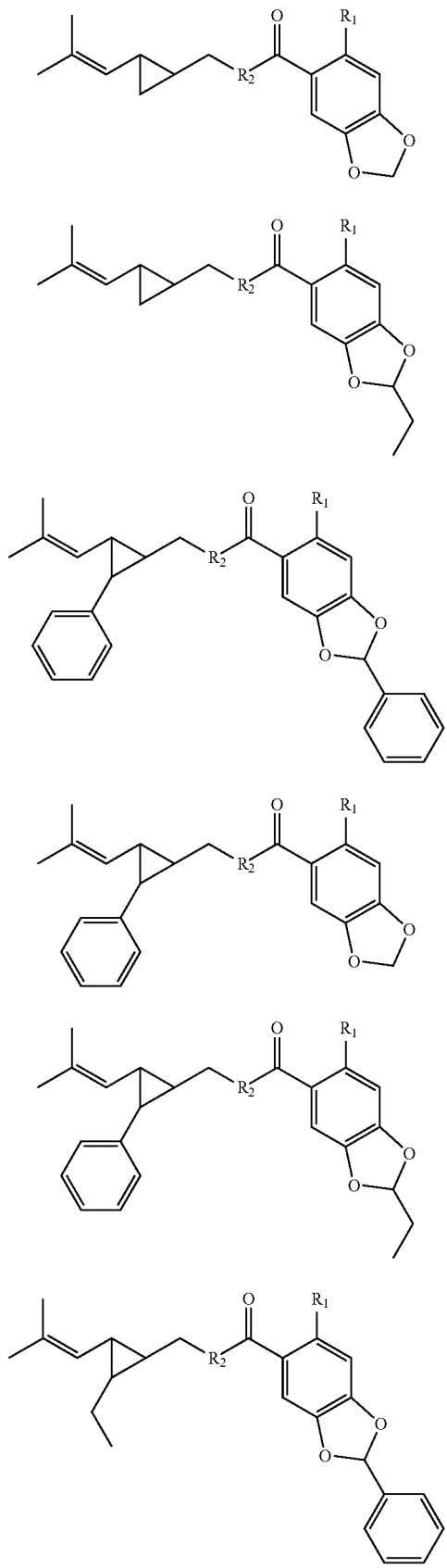

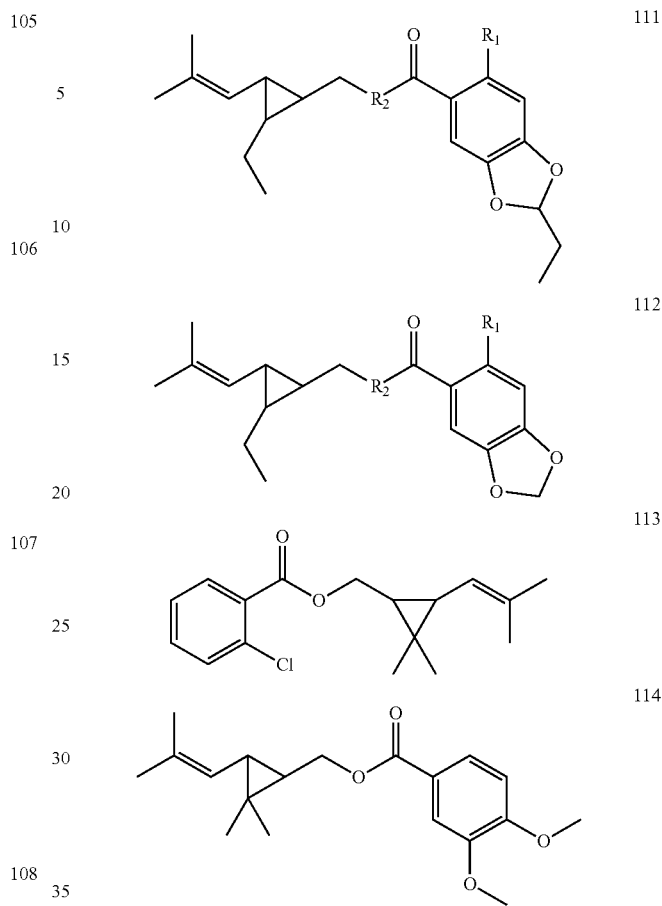

With respect to the captioned structures above, the present invention provides specific embodiments wherein $R_1$ is F, Cl, Br, I, H, $CH_3$ or Benzyl and $R_2$ is $CH_2$, NH or O, as listed below. For example, for compounds 101-112 disclosed above, specific embodiments are as follows:

a, $R_1$ is F and $R_2$ is $CH_2$;
b, $R_1$ is F and $R_2$ is NH;
c, $R_1$ is F and $R_2$ is O;
d, $R_1$ is Cl and $R_2$ is $CH_2$;
e, $R_1$ is Cl and $R_2$ is NH;
f, $R_1$ is Cl and $R_2$ is O;
g, $R_1$ is Br and $R_2$ is $CH_2$;
h, $R_1$ is Br and $R_2$ is NH;
i, $R_1$ is Br and $R_2$ is O;
j, $R_1$ is I and $R_2$ is $CH_2$;
k, $R_1$ is I and $R_2$ is NH;
m, $R_1$ is I and $R_2$ is O;
n, $R_1$ is H and $R_2$ is $CH_2$;
o, $R_1$ is H and $R_2$ is NH;
p, $R_1$ is H and $R_2$ is O;
q, $R_1$ is $CH_3$ and $R_2$ is $CH_2$;
r, $R_1$ is $CH_3$ and $R_2$ is NH;
s, $R_1$ is $CH_3$ and $R_2$ is O;
t, $R_1$ is Benzyl and $R_2$ is $CH_2$;
u, $R_1$ is Benzyl and $R_2$ is NH;
v, $R_1$ is Benzyl and $R_2$ is O;

From the disclosed generic structures and the chart above, examples of specific embodiments of the present invention such as 101a and 103m would be represented by the chemical formulas

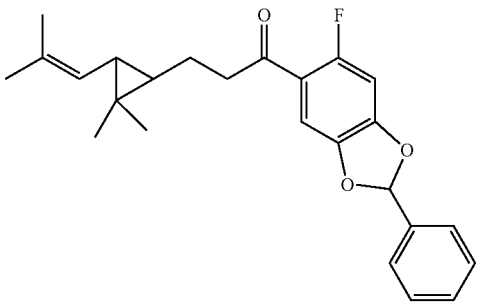

101a

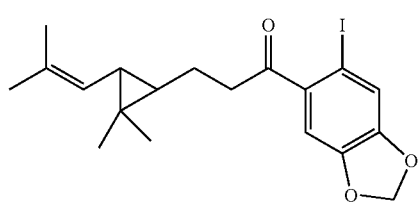

103m

Likewise, compounds 109c and 109h would be represented as follows:

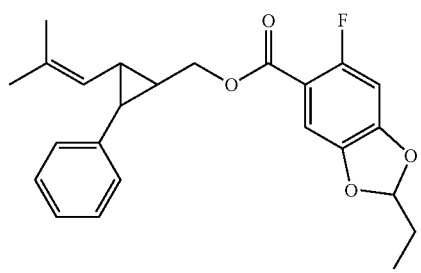

109c

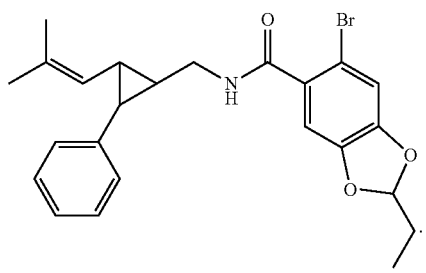

109h

In another embodiment, the present invention encompasses compounds and compositions and formulations for treating abnormal cell growth comprising contacting the cell or cells with at least one compound of Formula II:

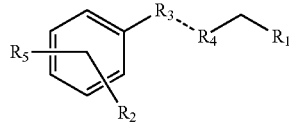

(II)

or pharmaceutically acceptable salts or prodrugs thereof, wherein $R_1$ is H; a halogen; —OH; an amine; a carboxyl; substituted or unsubstituted: cyclic or acyclic alkyl group, cyclic or acyclic alkenyl group, cyclic or acyclic akynyl group, carboxyalkyl, cyclic or acyclic alkoxy, aryl group, alkylaryl group, arylalkyl group, heteroaryl group, heteroalkyl group; $COR_8$; $CSR_8$; $SOR_8$; $SO_2R_8$; $CON(R_8)_2$; $CSN(R_8)_2$; wherein $R_1$ and $R_4$ can form a 3-10 membered ring with one or more of C, S, O or N;

$R_2$ and $R_5$ are each independently H; a halogen; —OH; an amine; a carboxyl; substituted or unsubstituted: cyclic or acyclic alkyl group, cyclic or acyclic alkenyl group, cyclic or acyclic akynyl group, carboxyalkyl, cyclic or acyclic alkoxy, aryl group, alkylaryl group, arylalkyl group, heteroaryl group, heteroalkyl group; $COR_8$; $CSR_8$; $SOR_8$; $SO_2R_8$; $CON(R_8)_2$; $CSN(R_8)_2$; or a monocyclic or polycyclic substituted or unsubstituted fused ring structure that is fused with the ring atoms to which either $R_2$ or $R_5$ are attached; wherein $R_2$ and $R_5$ can form a 3-10 membered ring with one or more of C, S, O or N;

$R_3$ and $R_4$ are each independently CH; $C(R_1)_2$; CO; $COR_1$; $CON(R_1)_2$; CS; $CSR_1$; $CS(R_1)_2$; $C(SR_1)R_1$; $CSNR_1$; SH; SO; $SO_2$; $S(O)R_1$; $S(O)(R_1)_2$; N; NH; $NR_1$; $NOR_1$; or O; wherein $R_3$ and $R_4$, together with the ring atoms to which $R_4$ is attached, can form an additional fused 5- or 6-membered ring structure, with one or more of C, S, O or N; wherein $R_2$ and $R_3$ together with the ring atoms to which they are attached, can form an additional fused 5- or 6-membered ring structure, with one or more of C, S, O or N; wherein $R_3$ together with the ring atoms to which it is attached, can form an additional fused 5- or 6-membered ring structure, with one or more of C, S, O or N;

$R_8$ is H; —OH; an amine; a carboxyl; substituted or unsubstituted: cyclic or acyclic alkyl group, cyclic or acyclic alkenyl group, cyclic or acyclic akynyl group, an aryl group, an alkylaryl group, an arylalkyl group, heteroaryl group, heteroalkyl group; or a halogen; and ----- is a single bond or a double bond, wherein if ----- is a double bond, $R_3$ and $R_4$ are independently CH, N or SH.

Illustrative embodiments of compounds of the present invention useful in methods for treating abnormal cell growth include but are not limited to compounds 201-216 as disclosed below.

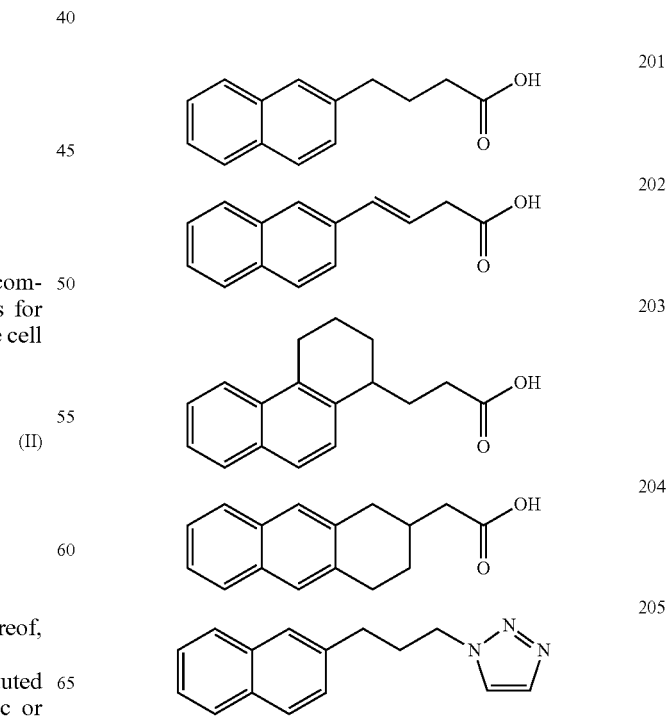

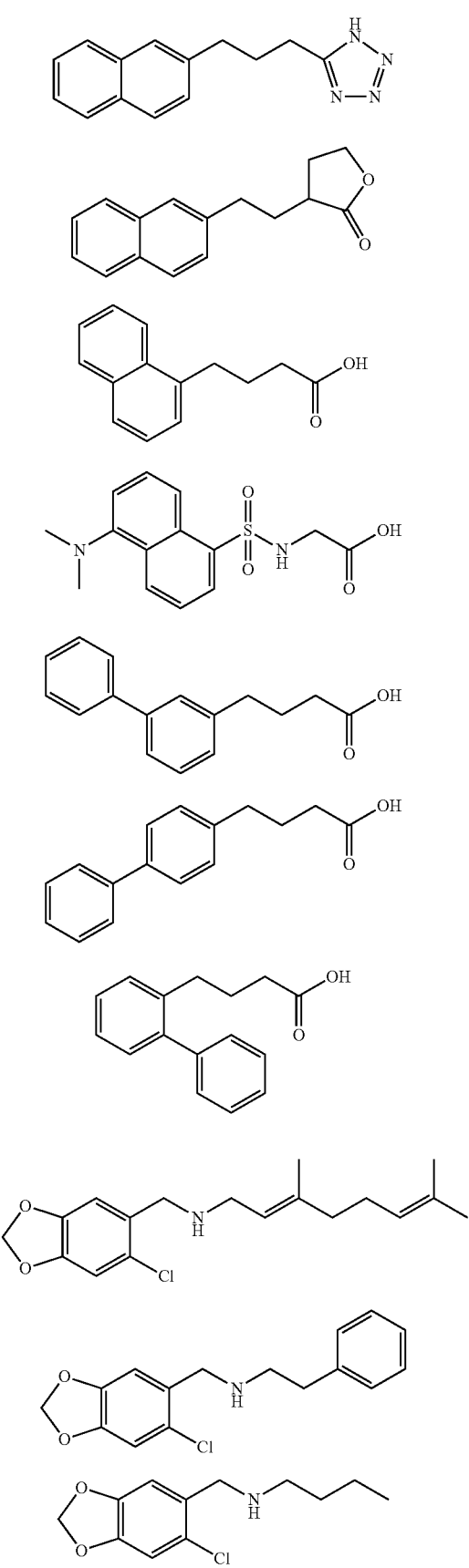

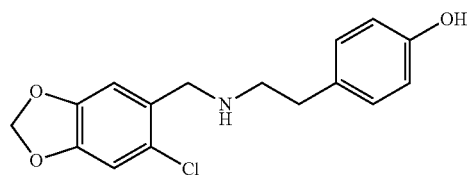

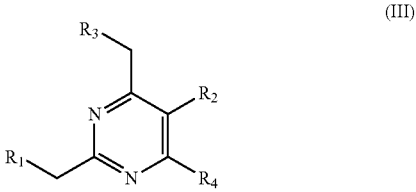

In another embodiment, the present invention encompasses compounds and compositions and formulations for treating abnormal cell growth comprising contacting the cell or cells with at least one compound of Formula III:

(III)

or pharmaceutically acceptable salts or prodrugs thereof, wherein $R_1$ and $R_3$ are each independently H; a halogen; —OH; an amine; a carboxyl; substituted or unsubstituted: cyclic or acyclic alkyl group, cyclic or acyclic alkenyl group, cyclic or acyclic alkynyl group, carboxyalkyl, cyclic or acyclic alkoxy, aryl group, alkylaryl group, arylalkyl group, heteroaryl group, heteroalkyl group; $COR_8$; $CSR_8$; $SOR_8$; $SO_2R_8$; $CON(R_8)_2$; $CSN(R_8)_2$; wherein $R_1$ and $R_3$ can form a 6-15 membered ring with one or more of C, S, O or N, $R_2$ and $R_4$ are each independently H; a halogen; —OH; an amine; a carboxyl; substituted or unsubstituted: cyclic or acyclic alkyl group, cyclic or acyclic alkenyl group, cyclic or acyclic akynyl group, carboxyalkyl, cyclic or acyclic alkoxy, aryl group, alkylaryl group, arylalkyl group, heteroaryl group, heteroalkyl group; $COR_8$; $CSR_8$; $SOR_8$; $SO_2R_8$; $CON(R_8)_2$; $CSN(R_8)_2$; wherein $R_2$ and $R_4$ can form a monocyclic or polycyclic 3-14 membered fused ring structure, together with the atoms to which they are attached, with one or more of C, S, O or N, and $R_8$ is —H; —OH; an amine; a carboxyl; substituted or unsubstituted: cyclic or acyclic alkyl group, cyclic or acyclic alkenyl group, cyclic or acyclic akynyl group, an aryl group, an alkylaryl group, an arylalkyl group, heteroaryl group, heteroalkyl group; or a halogen.

Illustrative embodiments of compounds of the present invention useful in methods for treating abnormal cell growth include but are not limited to compounds 301-307 and 308-314 as disclosed below.

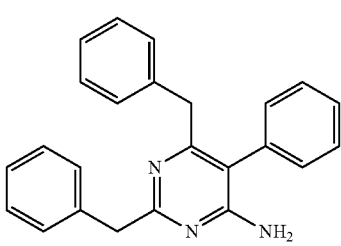

-continued

302
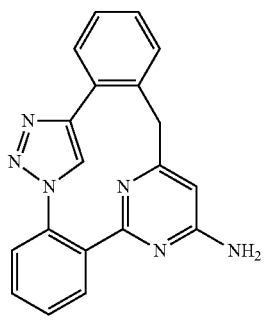

303
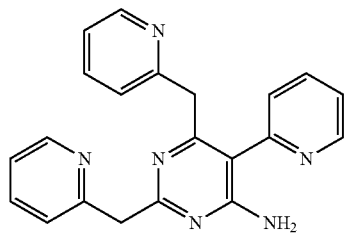

303a
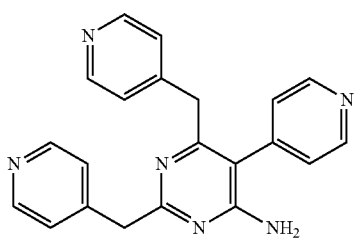

304
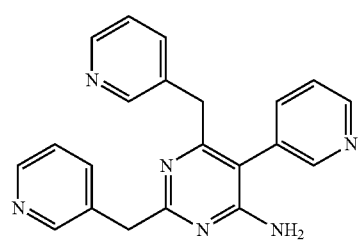

305
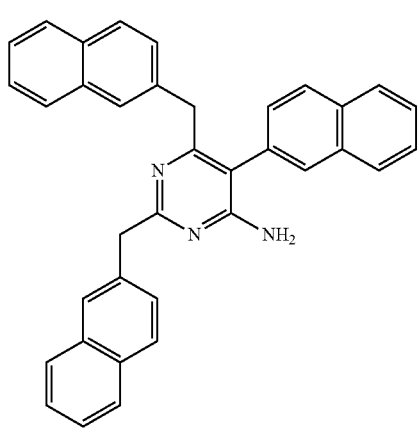

-continued

306
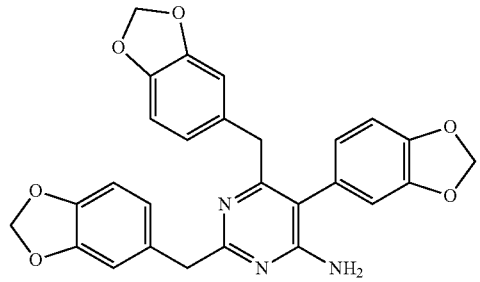

307
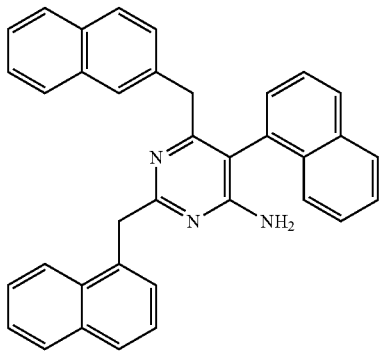

With respect to the compounds of 308, the present invention provides specific embodiments wherein $R_1$, $R_2$ and $R_3$, are each independently $NH_2$, OH, $OCH_3$, Cl, Br, $CH_3$, $CH(CH_3)_2$, $SO_2NH_2$, COOH, $CH_2CH_3$ or $CF_3$, as listed below.

308
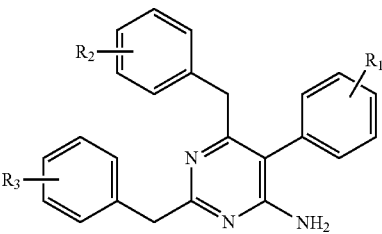

With respect to the compounds of 308, the present invention provides specific embodiments wherein $R_1$, $R_2$ and $R_3$, are each independently $NH_2$, OH, $OCH_3$, Cl, Br, $CH_3$ or $CF_3$. Additional embodiments of the present invention include compounds 309 and 310 below.

309
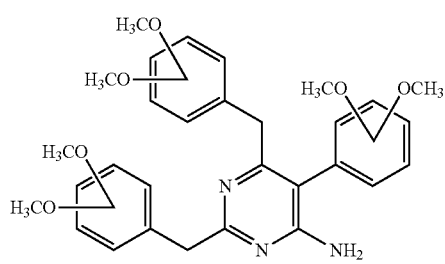

310
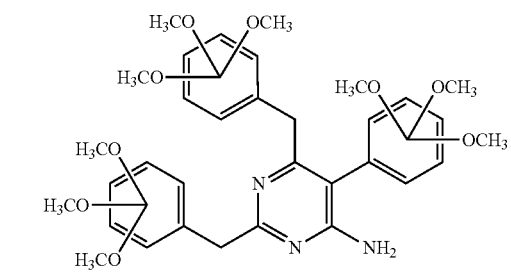
311
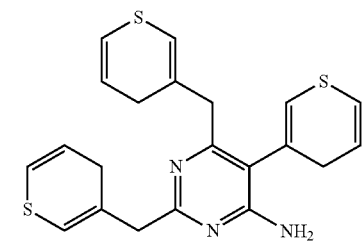
312
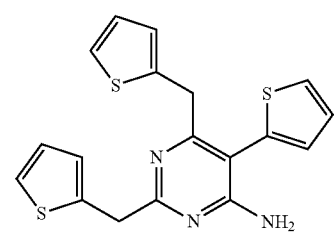
313
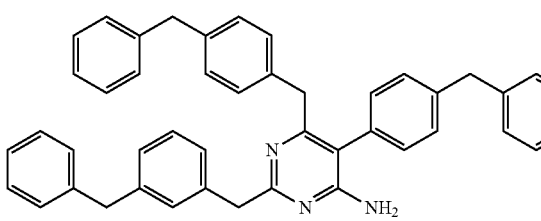
314
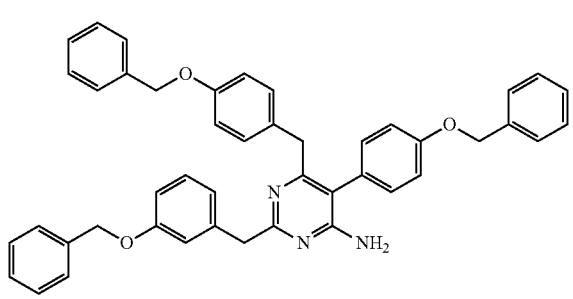
314-a
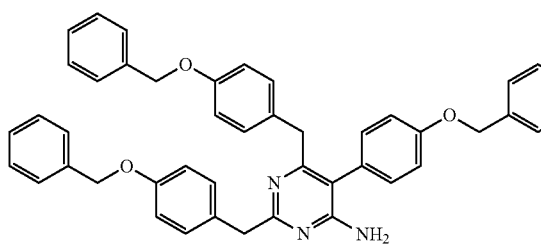
315
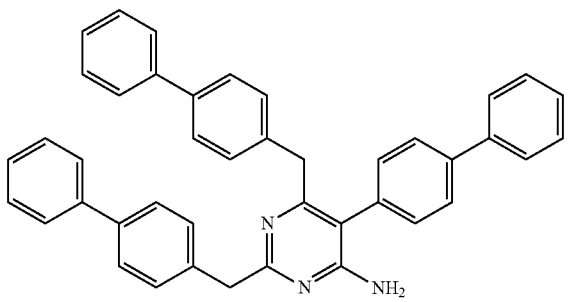
316
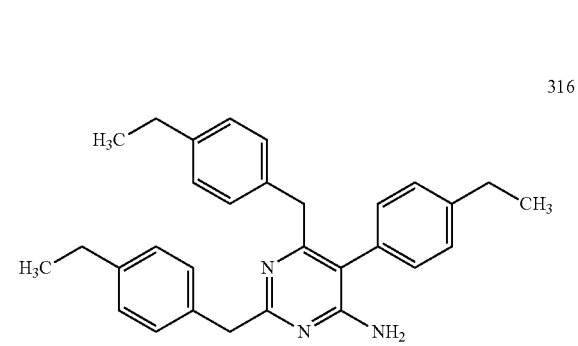
317
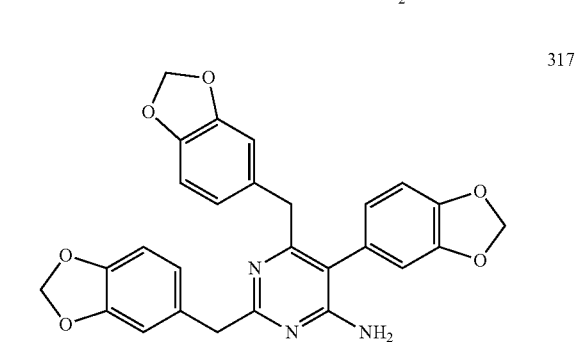
318
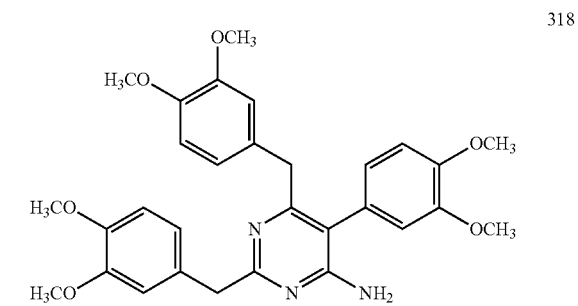
319
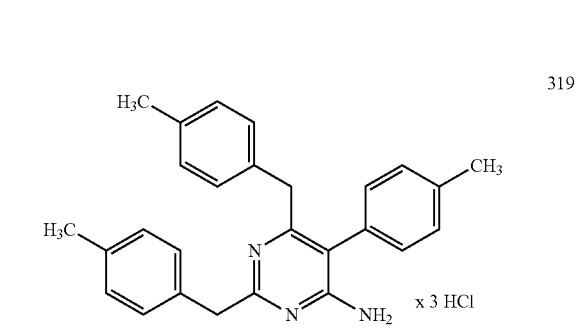
x 3 HCl

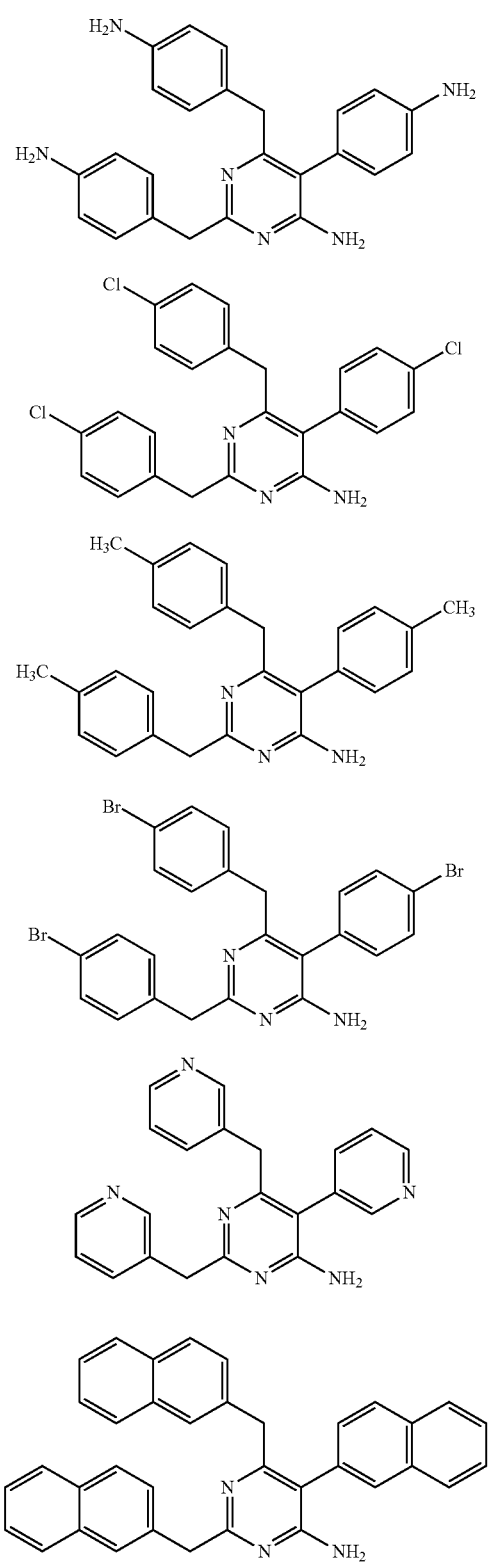

320

321

322

323

324

325

In select embodiments, the novel compounds of Formulas I, II and III do not encompass compounds 103f, 201, 301, 305 and 901-922 as these compounds that are explicitly excluded from the scope of novel compounds under Formulas I, II and III. All compounds of the present invention including compounds 103f, 201, 301, 305 and 901-922, however, can be used in the novel and inventive methods of treating abnormal cell growth as disclosed in the present invention.

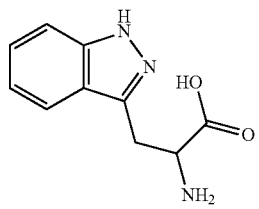

901

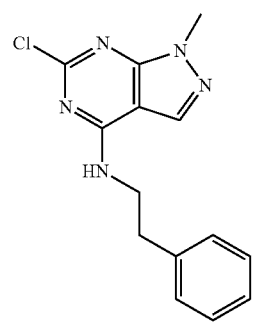

902

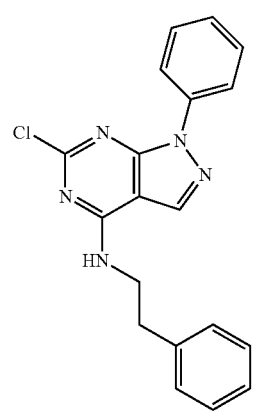

903

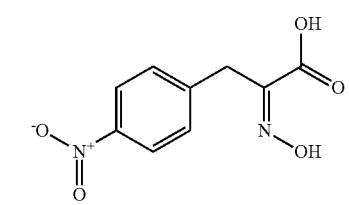

904

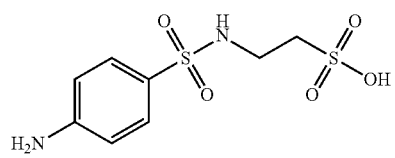

905

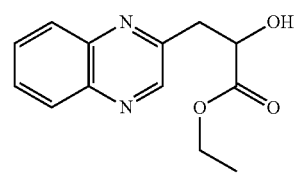

906

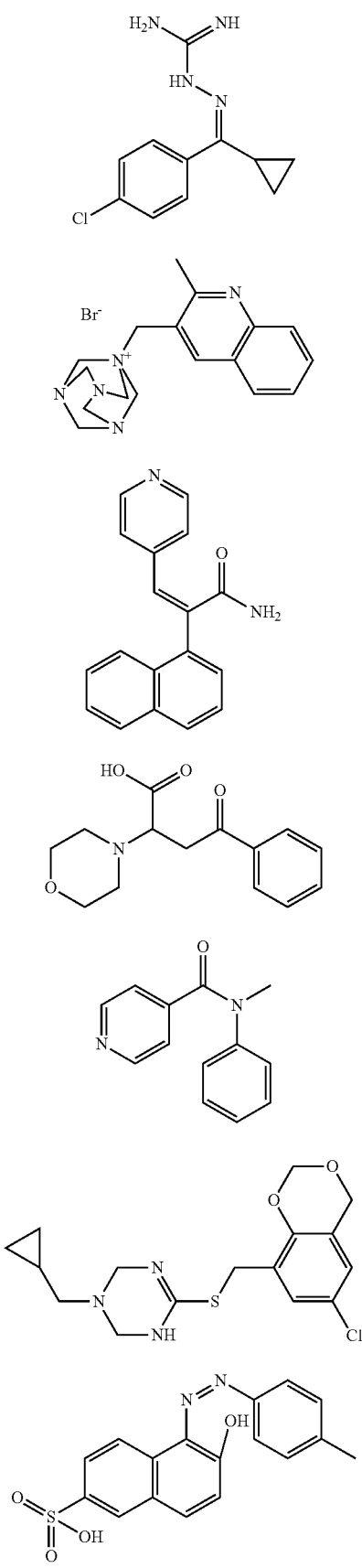
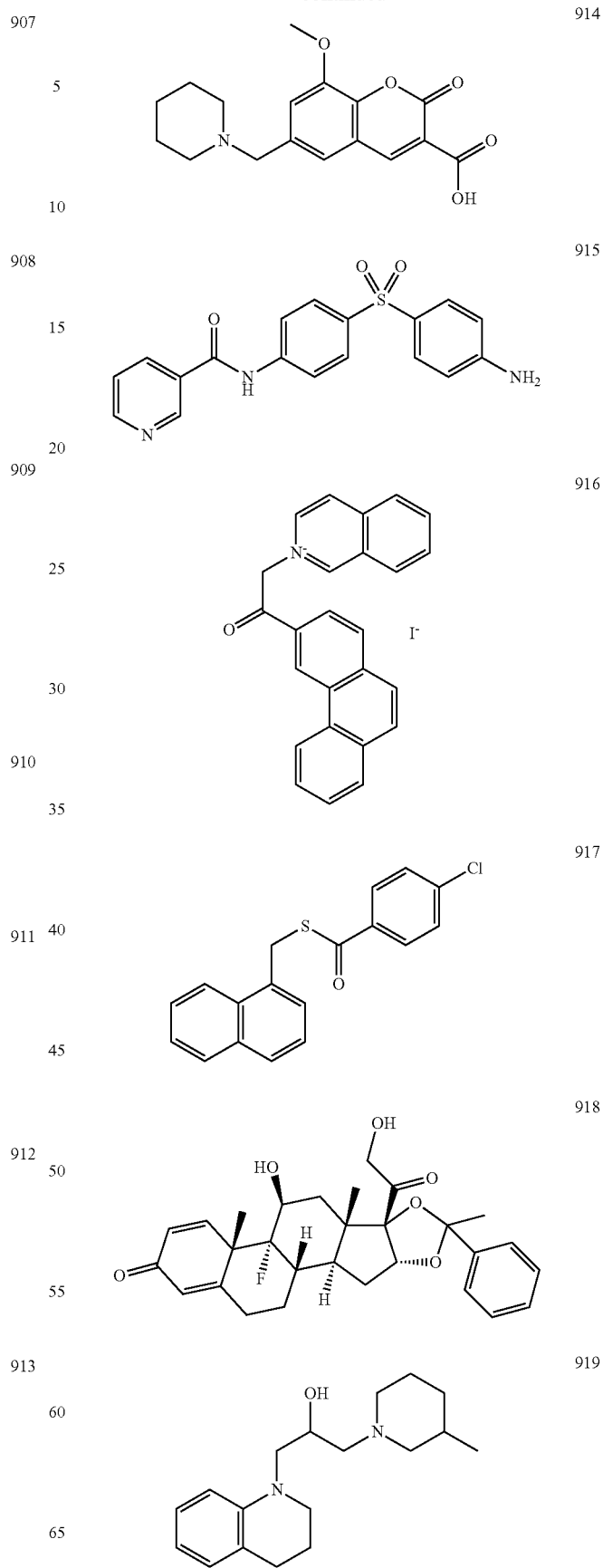

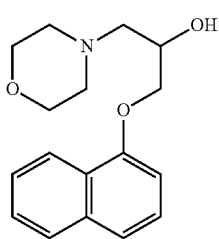

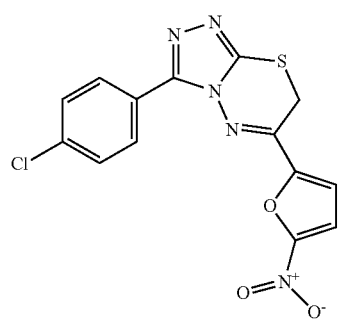

The compounds of the present invention can be synthesized by organic chemistry techniques known to those skilled in the art, as generally described by, but not limited to, the Schemes below.

Scheme 1—Rapid access to compounds of Formula I with two of the four possible stereochemical arrangements of the cyclopropane ring can be obtained by dicyclocarbodiimide-mediated coupling of 6-chloropiperonylic acid (3) with trans-chrysanthemyl alcohol (2a) or chrysanthemyl alcohol (2a) (below). To obtain other stereochemical arrangements of the cyclopropane ring system, however, Charette's catalyst (10) can be utilized for asymmetric cyclopropanation of mono-TBS (t-butyldimethylsilyl) protected 2-butenediol (4). Oxidation of the alcohol with TPAP (tetra-n-propylammonium perruthenate) followed by isopropylidene Wittig reagent and deprotection of the TBS group with TBAF (tetrabutylammonium fluoride) will yield the requisite alcohol (6) for coupling with 6-chloropiperonylic acid (3). The cis-cyclopropane system can be synthesized by an analogous route from mono-TBS protected Z-2-butenediol (7). Asymmetric cyclopropanation with Charette's catalyst (10) will give compound (8). TPAP oxidation, Wittig homologation, and TBAF-deprotection of the TBS group will give alcohol (9), which can also be conjugated with 6-chloro or 6-methyl piperonylic acid.

Finally, to incorporate the 1,1-dimethyl cyclopropane moiety with full stereocontrol, Evans' isopropyl chiral oxazolidinone auxiliary will be conjugated to senecioic acid to give compound (12). Rhodium mediated cyclopropanation with methyl diazoacetate should give a mixture of diastereomers (13), where the chiral auxiliary controls the facial selectivity of cyclopropanation, but the carbomethoxy group can be cis or trans to the carbonyl of the auxiliary, which should be a mixture separable by chromatography. Selective saponification of the methyl ester can be followed by TPAP oxidation to the aldehyde, Wittig homologation, and DIBAL-H (diisobutylaluminum hydride) reduction of the chiral auxiliary to the alcohol, to give compound (14) or (15).

Scheme 1

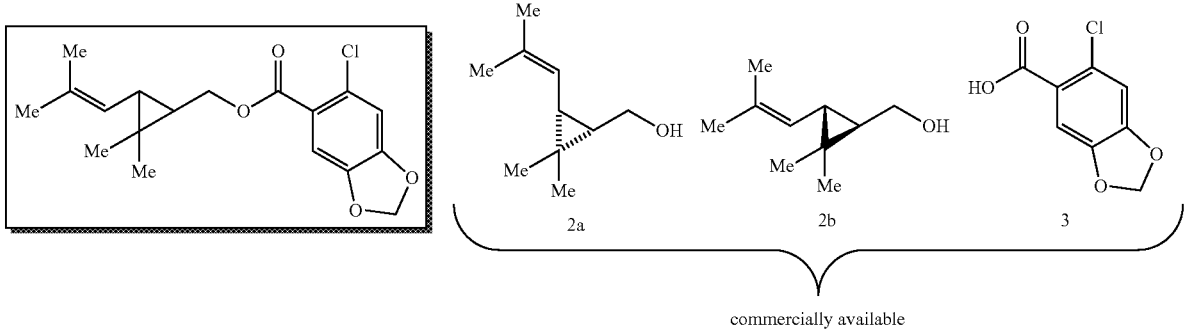

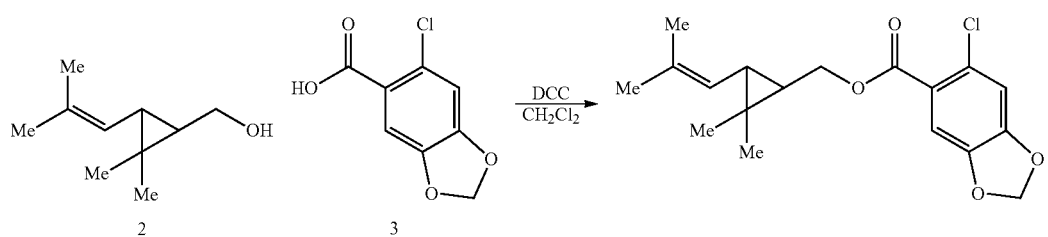

-continued
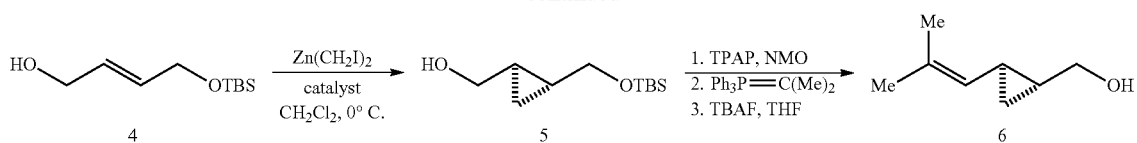
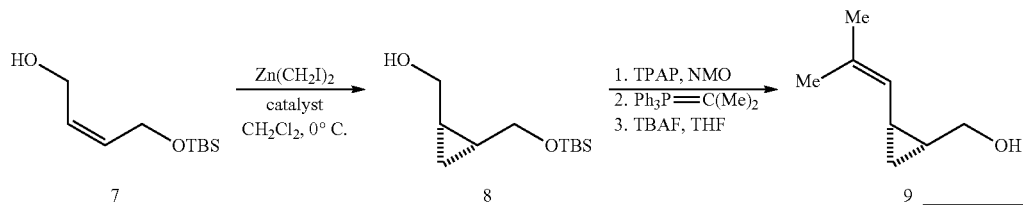
*J. Am. Chem. Soc.* 1998, 120, 11943-11952.
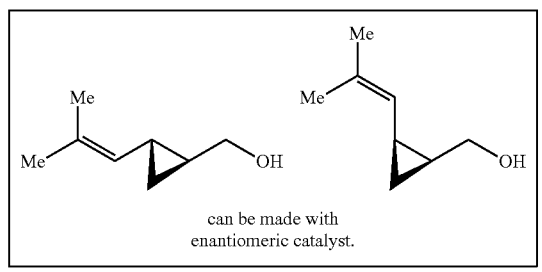
can be made with enantiomeric catalyst.
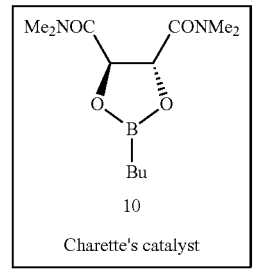
Charette's catalyst
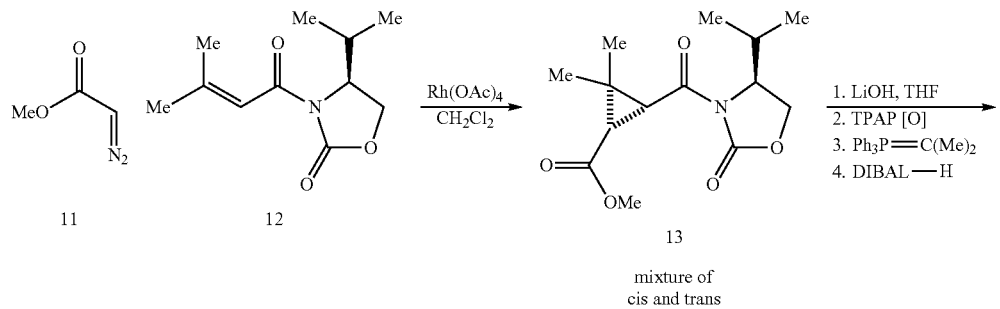
mixture of cis and trans
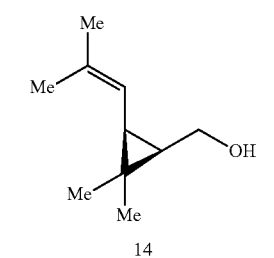
14
+
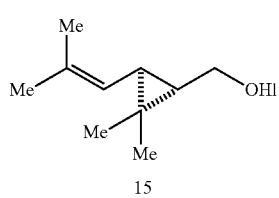
15
separable diastereomers Scheme 2—Compound (17) can be synthesized via a malonic ester synthesis from the available 2-bromomethyl-naphthalene (16) below. The 2-(2-iodo-ethyl)-naphthalene (18) is added to the dihydro-furan-2-one (19) to give compound (20). Using "click chemistry" the triazole (22) is synthesized from the azide (21). The acid (24) can be made from the 2-bromomethyl-biphenyl 23 via a malonic ester synthesis. Horner-Emmons chemistry is used to convert the ketone (25) into the (3,4-dihydro-1H-anthracen-2-ylidene)-acetic acid (26). Hydrogenation of (26) can provide one compound of the present invention (compound 204).

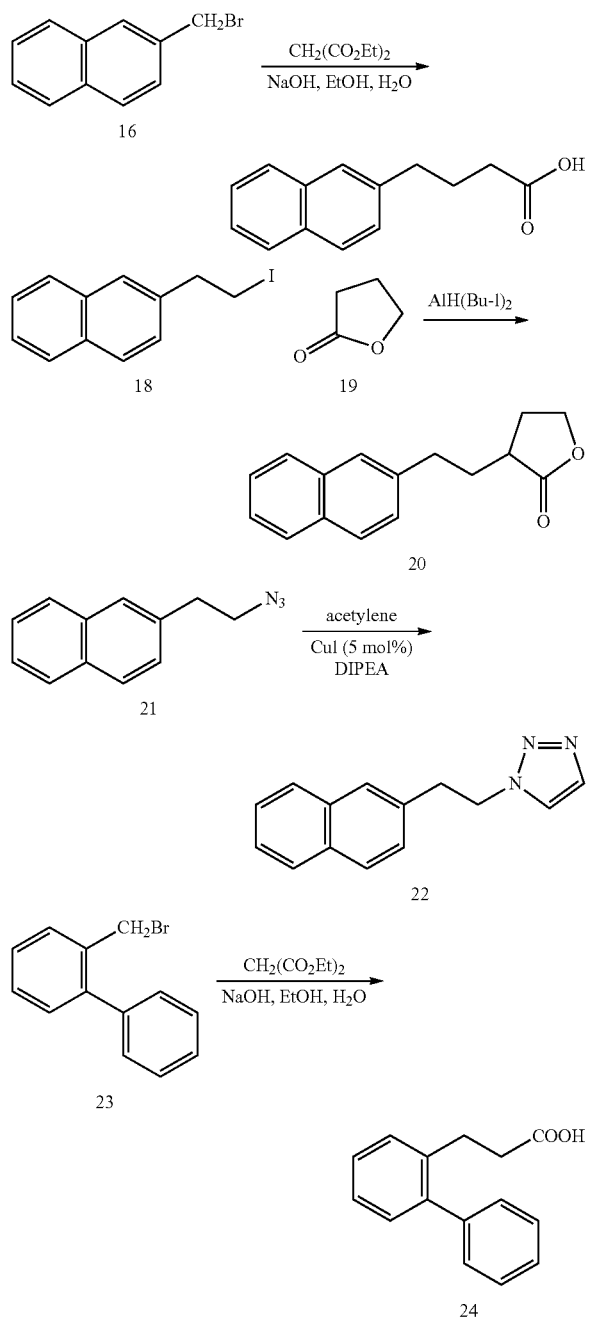

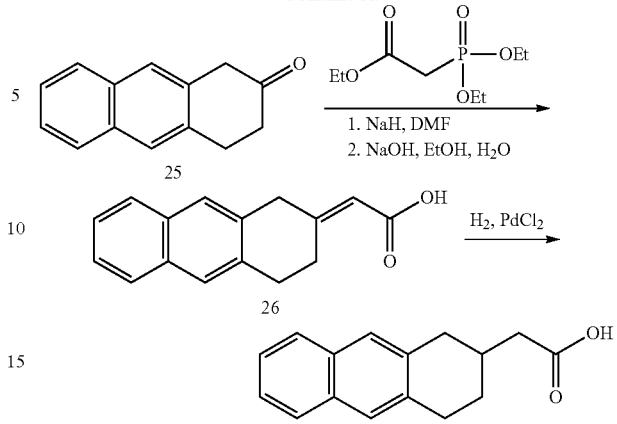

Scheme 3—The synthesis of symmetric analogs of 4-aminopyrimidines via trimerization of nitriles using microwave conditions is employed as described before (Baxendale, I. R., et al., J. Combin. Chem., 7:483-489 (2005)) and is incorporated by reference. To synthesize the proposed asymmetric aminopyrimidines, substituted benzamidines (30) are reacted with substituted 3-oxo-butyric acid methyl esters to give 2-phenyl-pyrimidin-4-ols (32). Analogs like (32) can be converted into the final substituted 4-aminopyrimidine (34). Alternatively, the 4-amino-2,6-dichloro-pyrimidine-5-carbonitrile (36) can be synthesized from 6-amino-2,4-dioxo-1,2,3,4-tetrahydro-pyrimidine-5-carbonitrile (35). Finally, the restricted analog (41) is made via a reaction of the azido-benzamidine (37) and the ester (38). Click chemistry affords the triazole (40) and is followed by conversion of (40) to the aminopyrimidine (41).

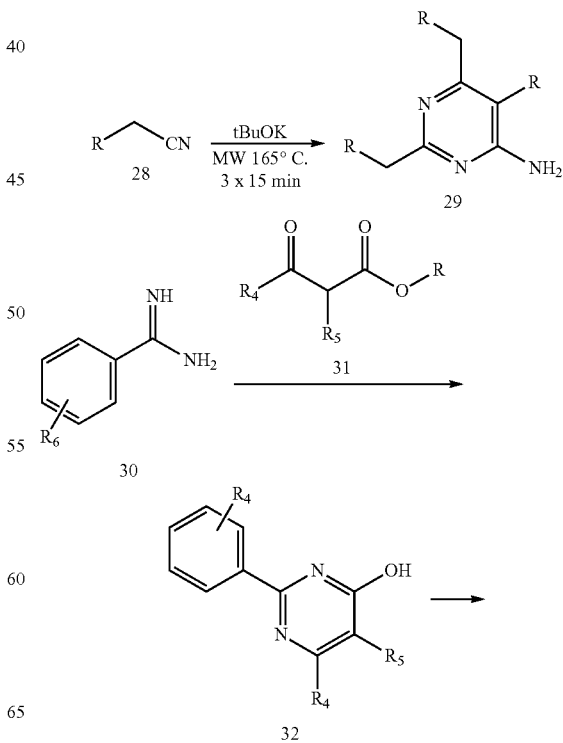

-continued

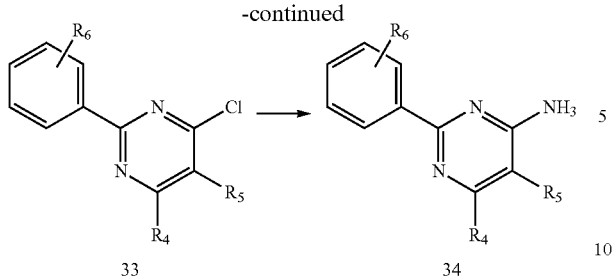

-continued

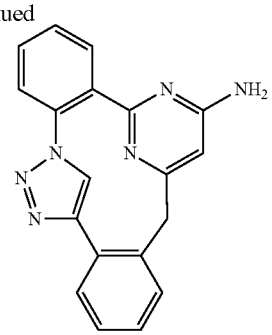

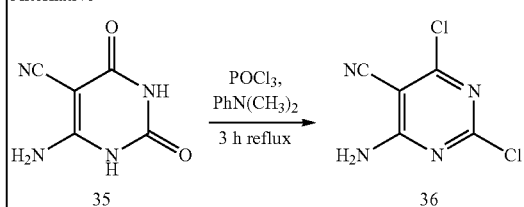

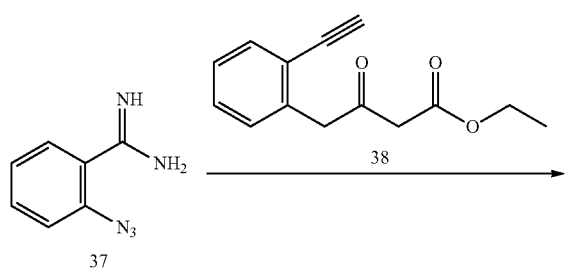

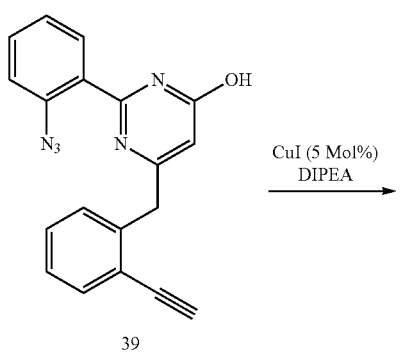

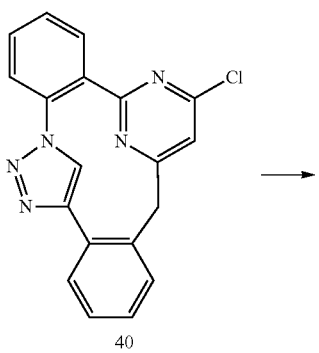

The compounds and compositions according to Formulas I, II or III of the present invention are useful in treating abnormal cell growth. In one embodiment, the abnormal cell growth is cancer or cancer cell growth or proliferation. As used herein and unless otherwise indicated, the terms "cancer" or "cancer cell" refer to abnormal cell growth or proliferation that may or may not include spontaneous or induced phenotypic changes. As used herein, "cancer" includes but is not limited to such abnormal conditions as hypertrophy, neoplasia, hyperplasia, benign and malignant cancer. As used herein, the term "tumor" is a general term that includes hypertrophies, neoplasias, hyperplasias, benign cancers and malignant cancers. Accordingly, certain embodiments of the present invention include but are not limited to treating a hypertrophy, a neoplasia, a hyperplasia, a benign or a malignant cancer in a subject. In additional embodiments, the present invention is directed to preventing or reducing the likelihood of metastasis and/or recurrence of a hypertrophy, a neoplasia, a hyperplasia, a benign or a malignant cancer within a subject comprising administering at least one compound of the present invention to the subject. For example, at least one compound of the present invention may be administered after tumor resection/removal/ablation, etc. to reduce the likelihood of recurrence of the tumor in the subject. In another example, at least one compound of the present invention may be administered to reduce the likelihood of metastasis of the tumor in the subject.

These methods include but are not limited to inhibiting or reducing the growth of a cancer cell or cells, such as lung cancer cell(s), breast cancer cell(s), colon cancer cell(s), malignant melanoma cell(s), ovarian carcinoma cell(s), brain tumor cell(s), soft tissue sarcoma cell(s), rhabdomyosarcoma cell(s), pancreatic cancer cell(s), prostate cancer cell(s) and osteosarcoma cell(s), which comprises administering to the cell a pharmaceutically effective amount of a composition comprising a compound of Formula I, II or III or a pharmaceutically acceptable salt or prodrug thereof.

The invention also encompasses a method of reducing the likelihood of cancer metastasis, such as lung cancer metastasis, breast cancer metastasis, colon cancer metastasis, malignant melanoma metastasis, ovarian carcinoma metastasis, brain tumor metastasis, soft tissue sarcoma metastasis, rhabdomyosarcoma metastasis, pancreatic cancer metastasis, prostate cancer metastasis and osteosarcoma metastasis, which comprises administering to a subject in need of such treatment a therapeutically effective amount of a composition comprising a compound of Formula I, II or III or a pharmaceutically acceptable salt or prodrug thereof.

In one embodiment, "treatment" or "treating" refers to an amelioration of a disease or disorder, or at least one detectable symptom thereof. In another embodiment, "treatment"

or "treating" refers to an amelioration of at least one measurable physical parameter, not necessarily discernible by the patient. In yet another embodiment, "treatment" or "treating" refers to inhibiting the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder.

In certain embodiments, the compositions of the invention are administered to a patient, for example a human, as a preventative measure against diseases, including preventing the occurrence or reoccurrence of a tumor or preventing or slowing the progression of a tumor.

As used herein, the term "prevent," as it relates to tumors and/or abnormal cell growth, indicates that a compound of the present invention is administered to a subject to at least partially inhibit the or reduce the likelihood of growth, division, spread, or proliferation of tumor cells. Thus a subject may be "pretreated," by administering the one or more compounds of the present invention to prevent tumors from arising. The phrase "preventing the progression," as it relates to tumors, is used to mean a procedure designed to at least partially inhibit the detectable appearance of one or more additional tumors or aberrant cell growth in a patient already exhibiting one or more symptoms of the presence of a tumor or aberrant cell growth, and is also used to mean at least partially prohibiting the already-present symptoms of cancer from worsening in the subject.

The compounds or compositions of the present invention can be used to treat abnormal cell growth by contacting the cell or cells with at least one compound or composition of the present invention. As used herein, the term "contact" when used with respect to when the compounds or compositions of the present invention are being used for the methods disclosed herein refers to the act of bringing the compounds or compositions in proximity with one another such that the compounds or compositions can exert their biological effects on the cell or cells. Bringing the compounds or compositions into contact with a cell or cells can mean applying the compounds or compositions directly onto the cells such as in an in vitro setting. Alternatively, bringing the compounds or compositions into contact with a cell or cells can mean administering the compounds or compositions to a subject or patient.

As used herein, the term "administer" and "administering" are used to mean introducing at least one compound or composition into a subject. When administration is for the purpose of treatment, the substance is provided at, or after the diagnosis of an abnormal cell growth, such as a tumor. The therapeutic administration of this substance serves to inhibit cell growth of the tumor or abnormal cell growth.

As used herein, the term "coadminister" is used to mean that each of at least two compounds are administered during a time frame wherein the respective periods of biological activity overlap. Thus the term includes sequential as well as coextensive administration of the compositions of the present invention. If more than one substance is coadministered, the routes of administration of the two or more substances need not be the same. The scope of the invention is not limited by the identity of the substance which may be coadministered with the compositions of the present invention. For example, one of the compounds of the present invention may be co-administered with another compound of the present invention or another other pharmaceutically active substances, such as *vinca* alkaloids, nucleic acid inhibitors, platinum agents, interleukin-2, interferons, alkylating agents, antimetabolites, corticosteroids, DNA intercalating agents, anthracyclines, and ureas. Examples of specific agents in addition to those exemplified herein, include hydroxyurea, 5-fluorouracil, anthramycin, asparaginase, bleomycin, dactinomycin, dacabazine, cytarabine, busulfan, thiotepa, lomustine, mechlorehamine, cyclophosphamide, melphalan, mechlorethamine, chlorambucil, carmustine, 6-thioguanine, methotrexate, etc.

Due to the activity of the compounds of the invention, the compounds are advantageously useful in veterinary and human medicine. As described above, the compounds of the invention are useful for the treatment or prevention of conditions caused by uncontrolled cell growth, hyperproliferation of cells, tumor growth, and cancers, for example, lung cancer, pancreatic cancer, leukemia, breast cancer, liver cancer, kidney cancer, human glioblastoma and prostate cancer.

The invention provides methods of treatment and prophylaxis by administration to a subject of a therapeutically effective amount of a composition comprising a compound of the invention. The subject can be a mammal, including, but is not limited to, an animal such a cow, horse, sheep, pig, chicken, cat, dog, mouse, rat, rabbit, guinea pig, non-human primate or human.

The present compositions, which comprise one or more compounds of the invention can be administered intravenously, intravenously intramuscularly intraperitonealy and orally.

Suitable dosage ranges of the compounds of the invention, regardless of the route of administration, are generally about 0.0001 milligram to 2000 milligrams of a compound of the invention per kilogram body weight. In one specific embodiment, the dose is about 0.001 milligram to about 1500 milligrams per kilogram body weight, more specifically about 0.01 milligram to about 1000 milligrams per kilogram body weight, more specifically about 0.1 milligram to about 500 milligrams per kilogram body weight, and yet more specifically about 1 milligram to about 100 milligrams per kilogram body weight.

The compounds and the compositions of the invention may also be administered by any other route, for example, by infusion or bolus injection, by absorption through epithelial or mucocutaneous linings (e.g., oral mucosa, rectal and intestinal mucosa, etc.), and they may be administered together with another biologically active agent. Administration can be systemic or local. Various delivery systems are known, e.g., encapsulation in liposomes, microparticles, microcapsules, capsules, etc., and can be used to administer a compound or composition of the invention. In certain embodiments, more than one compound of the invention is administered to a patient. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically. The preferred mode of administration is left to the discretion of the practitioner, and will depend in-part upon the site of the medical condition.

In specific embodiments, it may be desirable to administer one or more compounds or compositions of the invention locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as but not limited to silastic membranes, or fibers. In one embodiment, administration can be by direct injection at the site (or former site) of an atherosclerotic plaque tissue.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and vehicles such as triglycerides.

The present compositions will contain a therapeutically effective amount of a compound of the invention, optionally more than one compound of the invention, preferably in purified form, together with a suitable amount of a pharmaceutically acceptable vehicle so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the compounds of the invention and pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use.

In another embodiment, the compounds and/or compositions of the invention are formulated in accordance with routine procedures as a pharmaceutical composition adapted for intravenous administration to human beings. Typically, compounds and/or compositions of the invention for intravenous administration are solutions in sterile isotonic aqueous buffer. Where necessary, the compositions may also include a solubilizing agent. Compositions for intravenous administration may optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound of the invention is to be administered by infusion, it can be dispensed, for example, with an infusion bottle containing sterile pharmaceutical grade water or saline. Where the compound of the invention is administered by injection, an ampoule of sterile water for injection or saline can be provided so that the ingredients may be mixed prior to administration.

In one specific embodiment, the compositions of the invention can be administered orally. Formulations for oral delivery may be in the form of tablets, lozenges, aqueous or oily suspensions, granules, powders, emulsions, capsules, syrups, or elixirs, for example. Orally administered compositions may contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds of the invention. In one particular platform, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

The amount of a compound of the invention that will be effective in the treatment of a particular disorder or condition disclosed herein will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each patient's circumstances. In specific embodiments of the invention, the oral dose of at least one compound of the present invention is about 0.01 milligram to about 100 milligrams per kilogram body weight, or from about 0.1 milligram to about 50 milligrams per kilogram body weight, or from about 0.5 milligram to about 20 milligrams per kilogram body weight, or from about 1 milligram to about 10 milligrams per kilogram body weight.

Suitable dosage ranges for parenteral, for example, intravenous (i.v.) administration are 0.01 milligram to 100 milligrams per kilogram body weight, 0.1 milligram to 35 milligrams per kilogram body weight, and 1 milligram to 10 milligrams per kilogram body weight. Suitable dosage ranges for intranasal administration are generally about 0.01 pg/kg body weight to 1 mg/kg body weight. Suppositories generally contain 0.01 milligram to 50 milligrams of a compound of the invention per kilogram body weight and comprise active ingredient in the range of 0.5% to 10% by weight. Recommended dosages for intradermal, intramuscular, intraperitoneal, subcutaneous, epidural, sublingual, intracerebral, intravaginal, transdermal administration or administration by inhalation are in the range of 0.001 milligram to 200 milligrams per kilogram of body weight. Suitable doses of the compounds of the invention for topical administration are in the range of 0.001 milligram to 1 milligram, depending on the area to which the compound is administered. Effective doses may be extrapolated from dose-response curves derived from in vitro or animal model test systems. Such animal models and systems are well known in the art.

In other embodiments, a composition of the invention for parenteral, for example, intravenous administration includes about 0.001 milligram to about 2000 milligrams of a compound of the invention, more preferably about 0.01 milligram to about 1000 milligrams of a compound of the invention, more preferably about 0.1 milligram to about 500 milligrams of a compound of the invention, and yet more preferably about 1 milligram to about 200 milligrams of a compound of the invention.

The invention also provides pharmaceutical packs or kits comprising one or more containers filled with one or more compounds of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a certain embodiment, the kit contains more than one compound of the invention.

The compounds of the invention can be assayed in vitro and in vivo, for the desired therapeutic or prophylactic activity, prior to use in humans. For example, in vitro assays can be used to determine whether administration of a specific compound of the invention or a combination of compounds of the invention can be used for treating a particular disorder or condition disclosed herein. The compounds of the invention may also be demonstrated to be effective and safe using animal model systems.

Other methods will be known to the skilled artisan and are within the scope of the invention.

EXAMPLES

Example 1

Purified recombinant proteins BRCA1 (1-100), ER-α (337-379), ER-α (282-420), and ER-α (421-595) using various tags (GST, His, and Thioredoxin) have been successfully produced. BRCA1 (101-200), BRCA1 (1-200), and ER-α (282-595) can also be produced.

Surface Plasmon Resonance (SPR)-based biophysical assays (Biacore) of the compounds of the present invention can be used to assess real-time kinetics of molecular interaction. Drug screening can be performed directly from 96-well plates seeded with any of the compounds of the present invention. First, an SPR study will be used to assess the interaction of BRCA1 and ER-α and determine which fragments of each protein are best suited for the Biacore screening study. The binding sites of BRCA1 have been mapped to the N-terminus of BRCA1 (within aa 1-100 and secondarily aa 101-200) and the AF-2/LBD region of ER-α (aa 282-420 with some contributions from aa 421-595). BRCA1 (1-100, 101-200, and 1-200), and ER-α (282-420 and 282-595) are used to confirm the physical interaction of the fragments of the two proteins and determine the kinetics using Biacore. A combination of two fragments that best maintain the high affinity BRCA1: ER-α interaction is selected for screening.

Example 2

To determine the effects of test compounds on cathepsin D and pS2 expression, MCF-7 or T47D cells are cultured in DMEM containing 5% charcoal-stripped serum (CSS) and are treated with and without estradiol (E2) (10 nM) in the presence of either vehicle (DMSO) only, test compounds or known inactive compounds for about 24 hours and harvested for RNA and protein assays. Cathepsin D and pS2 mRNA levels are determined by quantitative qRT-PCR; and the protein levels will be determined by Western blotting. As a positive control for inhibition of cathepsin D and pS2, cells are transfected with wtBRCA1 or empty pcDNA3 vector and then tested for E2-stimulated cathepsin D and pS2 expression. The BRCA1 and ER-α protein levels are monitored by Western blotting.

MCF-7 cells are first incubated in DMEM containing 5% CSS for 72 hours, with daily washing with fresh medium to remove E2 that may be stuck to cells. Cells are then treated with or without E2 at several different time points, e.g., 15, 30, 60, and 120 min, in the presence of a test compound, a known inactive compound or vehicle (DMSO) and subsequently harvested for chromatin immunoprecipitation (ChIP) assays to assess the content of ER-α and BRCA1 at the estrogen response element (ERE) of the cathepsin D promoter. As a negative control, assays are carried out using PCR primers corresponding to a region of the cathepsin D promoter distant from the ERE. For comparison, similar experiments are performed on cells transfected with wtBRCA1 or pcDNA3 vector. The total cellular levels of ER-α and BRCA1 are monitored by Western blotting.

Example 3

Another possible application of the compounds of the present invention is in combination with other anti-estrogens (or other agents such as chemotherapy drugs or signal transduction inhibitors), particularly if the combinations of agents act synergistically but have different toxicities. An example might be a combination of BRCA1-mimetic plus Tamoxifen to overcome the pro-estrogenic activity of Tamoxifen in the endometrium.

Tamoxifen alone stimulates ERE-TK-Luc reporter activity in MCF-7 cells, while it inhibits estradiol (E2)-stimulated reporter activity. Knockdown of BRCA1 shifts the balance of Tamoxifen activity from that of an ER-α antagonist towards that of an agonist, suggesting that BRCA1 regulates the antagonist vs. agonist properties of Tamoxifen.

Briefly, MCF7 or T47D cells are transfected overnight with an ERE-TK-Luc reporter construct. An ERE-TK-Luc construct contains an estrogen response element (ERE) upstream of a minimal thymidine kinase (TK) promoter that drives the expression of the luciferase (Luc) reporter gene. After transfection, the cells are subsequently washed and allowed to recover for several hours. The cells are then incubated with and without E2 (at about 10 nM) along with the agent(s) to be tested for 24 hours. The agents and combinations to be tested are: group 1) vehicle; group 2) test compound; group 3) Tamoxifen; group 4) Fulvestrant; group 5) test compound+Tamoxifen; and group 6) test compound+Fulvestrant. The cells are subsequently harvested for luciferase reporter assays. The end-points are the ability of the combination (groups 5 and 6) to inhibit E2-stimulated reporter activity compared to each agent alone. Different concentrations of each agent are tested, with the goal of documenting synergy for potentiation or inhibition of E2-stimulated reporter activity (if it occurs) by showing that the test compound at a concentration that is ineffective by itself can potentiate the ER-α inhibitory activity of Tamoxifen or Fulvestrant (or vice versa), and/or that combinations of the test compound and Tamoxifen or Fulvestrant at concentrations for which each agent is ineffective by itself can significantly inhibit E2-stimulated ER-α activity.

If a combination of a test compound plus Tamoxifen or Fulvestrant can synergistically inhibit E2-stimulated ER-α activity, this combination can also be tested to inhibit E2-stimulated MCF-7 cell proliferation.

Example 4

Three compounds were tested for their ability to inhibit ER-α activity. Briefly, compounds 103(f), 201 and 301 were tested for their ability to inhibit E2-stimulated ER-α transcriptional activity in MCF-7 cells utilizing the ERE-TK-Luc reporter to obtain a readout of ER-α activity. This has proved to be a reliable and reproducible assay of ER-α activity in many prior studies. A dose of 10 nM of E2 (17β-estradiol) was utilized to stimulate ER-α activity. This dose yielded about a 20-150-fold increase in ERE-TK-Luc activity, and a wtBRCA1 expression vector reduced the E2-stimulated ER-α activity by ≥99%, as compared with empty pcDNA3 vector or a sham transfection control. Initially, each compound was tested at doses of 1 µM and 50 µM.

The values of $IC_{50}$ and $IC_{80}$ (concentrations required for inhibition of ER-α activity by 50% and 80%, respectively) are summarized in the Table below.

| Compound | $IC_{50}$ (µM) | $IC_{80}$ (µM) |
| --- | --- | --- |
| 103(f) | 3 | 5 |
| 301 | 12 | 40 |
| 201 | 4 | 50 |

Like breast cancer, endometrial cancer development is E2-dependent, and women that carry BRCA1 mutations exhibit a significantly increased risk for endometrial cancer. For reasons that are not well understood, Tamoxifen acts as an ER-α agonist in the uterus, where it stimulates the development of endometrial hyperplasia and carcinoma. Compounds 103(f) and 301 were tested to determine if they antagonize E2-stimulated ER-α activity in endometrial cancer cells as they do in breast cancer cells. Three endometrial carcinoma cell lines (CRL2923, CRL1671, and CRL1622), all of which were obtained from the American Type Culture Collection, were tested. One of these cell lines is ER-positive (CRL2923), while the other two are ER-negative. For the two ER-negative cell lines, a wild-type ER-α expression vector was co-transfected along with the ERE-TK-Luc reporter to allow measurement of E2-stimulated ER-α transcriptional activity. In all three cell lines tested, compounds 103(f) and 301 each effectively inhibited E2-stimulated ER-α activity, with residual activity levels ranging from 11-25% at a concentration of 50 M (P<0.001). In these assays, E2-stimulated ER-α activity in the absence of drug ranged from about 30-fold to about 80-fold, indicating a robust stimulation of ER-α activity similar to that obtained in breast carcinoma cells at an E2 concentration of 10 nM.

Compound 103(f) was tested for its effect on E2 stimulated proliferation of MCF-7 cells. Briefly, cells were inoculated into 12-well dishes at $1 \times 10^4$ cells per well on day 0 in 5% charcoal-stripped serum (CSS). On day 1, after allowing for cell attachment, the cells were refed fresh medium containing 2% CSS with or without estradiol (E2) (10 nM) and either with vehicle (DMSO), 103(f) (5 µM or 20 µM). Triplicate wells were counted on days 1-4 to determine the effect of 103(f) on cell growth. Cells treated with DMSO only continued to grow slowly and reached a density of about $4 \times 10^4$ cells per well by day 4, while cells treated with (DMSO+E2) grew much more rapidly and reached $9 \times 10^4$ cells per well by day 4 (P<0.01, two-tailed t-test). Compound 103(f) alone (5 µM or 20 µM) had little or no effect on cell growth, as compared with DMSO, but in the presence of E2, compound 103(f) at either dose blocked most of the E2-stimulated cell growth (P<0.01).

Example 5

A number of cell lines have been developed to investigate the mechanisms of anti-estrogen resistance. MCF-7/5-23, GI-101A, ZR-75-9a1, LY2, LCC2, and LCC9 are well-known examples of ER-α+ breast cancer cell lines that are resistant to Tamoxifen and in some cases, other anti-estrogens, e.g., Fulvestrant. In some cell lines, e.g., LCC9, knockdown of ER-α using siRNA inhibits cell proliferation, suggesting that ER-α contributes to cell proliferation even though the cells are Tamoxifen-resistant. To determine if the compounds of the present invention are active in cell lines that are resistant to Tamoxifen or Fulvestrant, a set of MCF-7 derived cell lines with different E2 and anti-estrogen sensitivities can be used. For example, some cell lines are listed below:

| Cell Line | ER-α Status | Response to Tamoxifen | Response to Fulvestrant | Response to Estradiol(E2) |
| --- | --- | --- | --- | --- |
| MCF-7 | + | Sensitive | Sensitive | E2-responsive; E2-dependent growth |
| LCC1 | + | Sensitive | Sensitive | Partially E2-depenedent growth |
| LCC2 | + | Resistant | Sensitive | E2-dependent growth |
| LCC9 | + | Resistant | Resistant | E2-insensitive growth; some E2-responsive components |

LCC1, LCC2, and LCC9 are routinely maintained in phenol red-free DMEM containing 5% CSS (available from the Tissue Culture Core, Lombardi Cancer Center, Georgetown University Medical Center). MCF-7 (original) cells are cultured under normal conditions in DMEM containing 5% fetal calf serum. To test the effects of various compounds of the present invention on the growth of LCC1/2/9, cells are seeded into 6-well dishes in phenol red-free DMEM with 5% CSS, allowed to attach for 24 hours and incubated with the test compound(s) for up to 6 days. MCF-7 cells are pre-incubated for at least 72 hours in phenol red-free DMEM with 5% CSS with daily washing prior to addition of compounds. Triplicate wells are counted on days 0, 2, 4, and 6, and each experiment is performed at least three times for reproducibility. The agents to be tested include: (1) vehicle only (DMSO), (2) test compound (5 and 20 µM), (3) known inactive compound, (4) test compound in (2) and E2 (10 nM), and (5) known inactive compound in (3) and E2. Other known anti-estrogens, e.g., Tamoxifen (1 µM) or Fulvestrant (100 nM), can be used as control on the effects of the test compounds on cell proliferation.

Example 6

A major function of BRCA1 is to promote error-free DNA double-strand break (DSB) repair by homologous recombination. The effect of test compounds of the present invention on DSB repair can be tested by transfection of a plasmid [HR-EGFP/3'-EGFP] that results in EGFP production when activated by DSB repair via homologous recombination.

MCF-7 cells are co-transfected with wtBRCA1 or pcDNA3 vector to determine the effect of the compounds on basal and BRCA1-stimulated DSB repair. The cells are then incubated with test compounds at various concentrations or DMSO for about 3 or 4 days to determine the effect of the compound on the recombination frequency.

BRCA1 over-expression protects cells against, and its knockdown sensitizes cells to, oxidative stress in part by stimulating the activity of the antioxidant transcription factor NFE2L2. Test compounds are tested for their capacity to interfere with the ability of wtBRCA1 to protect MCF-7 or T47D cells against oxidants ($H_2O_2$ and paraquat), using MTT assays to quantify cytotoxicity. The compounds can also be tested for their ability to inhibit wtBRCA1 stimulation of NFE2L2 activity using the NQO1-ARE-Luc reporter to measure NFE2L2 activity via the antioxidant response element (ARE).

Example 7

Dose range of the test compounds can be based on solubility, which can affect the choice of vehicle, route, volume, and maximum achievable dose for each compound. Generally, intraperitoneal (ip) is a first choice as a route of administration, as the total volume (and hence dose) deliverable is greatest. A subcutaneous (sc) depot or intravenous (iv) injection are alternatives. All drug preparations are sterilized by filtration prior to delivery. For aqueous soluble drugs, phosphate-buffered physiological saline at pH 7.4 is a standard vehicle. Ethanol and DMSO are used for less water-soluble agents, and cremaphore can be used for highly water-insoluble drugs. The choice of vehicle is often dose limiting for drugs that have little inherent toxicity, since vehicle toxicity can limit the maximum deliverable dose of drug.

To assess toxicity, a small drug-scaling analysis in intact, normal (not immune-compromised) female NCr mice (our standard strain) is performed. The primary goal is to establish a maximum tolerated dose (MTD) below which all subsequent activity studies will be performed. A change in the rate of weight gain is used as the initial measure of toxicity. Animals are monitored for behavioral or other changes that can indicate toxicity, e.g., somnolescence, limited mobility, hunching, and general change in appearance consistent with poor health. Some types of toxicity, however, may be transient and resolve within a few hours. Doses are increased at 10-fold increments until evidence of toxicity (toxic dose) is observed or the maximum deliverable dose is achieved. The highest dose that yields no detectable toxicity is the initial MTD estimate.

Blood is collected from treated animals in heparinized tubes, centrifuged, and the serum stored at −80° C. All tissues are removed at necropsy, visually examined, and placed in formalin. Subsequently, formalin-fixed tissues can be embedded in paraffin, sectioned, stained with H & E, and examined by a pathologist. Serum is used for standard blood chemistry or to measure several relevant end-points that might be affected by ER-α modulators, e.g., serum HDL- and LDL-cholesterol and triglycerides.

Doses at which body weight change or other physiologic/behavioral toxicity occurs are compared with those doses at which blood chemistry changes or gross or microscopic anatomic changes in tissues occur. The MTD may be adjusted downward if changes are detected in these end-points at doses lower than those utilizing the less sensitive physiologic/behavioral end-points. These studies may also provide some insight into the potential mechanisms of toxicity.

Example 8

In vivo activity studies will be performed in 4-6 week old female (ovariectomized) NCr athymic nude (nu/nu) mice. Animals receive mammary fat pad inocula (orthotopic) of tumor cell suspensions, e.g., MCF-7 cells since these cells are E2-dependent and allow for the direct testing of the test compounds on ER-α regulation of cell survival in vivo. Mice are given a single inoculation of $5 \times 10^6$ tumor cells in ≤100-μl of cell culture growth medium. The mice are implanted subcutaneously with a 17β-estradiol (0.72 mg)/60-day release pellet (Innovative Research of America) 48-hr before inoculation of tumor cells, to allow MCF-7 cell growth.

Example 9

The end-points include specific tumor growth delay, tumor incidence, and tumor doubling time. Tumor area is recorded every 2-3 days by measuring the longest axis and perpendicular width. Tumor doubling time (Td) is estimated following Gompertzian transformation. At the end of each experiment, the organs and tumors are removed for histopathological examination. For specific tumor growth delay in vivo, the times taken for both treated (T) and control (C) tumors to reach a predetermined size are measured. The growth delay is measured as (T-C)/C where the T/C or T-C values are median values. Repeated measures ANOVA are used to compare tumor size at each time point across the analysis and/or tumor doubling times are estimated and compared. Td values are compared by either one-way or multivariate ANOVA. Tumor latency and specific growth delay are explored using the Kaplan-Meier approach, and differences among groups tested by the Log-Rank test. Tumor incidence data (proportion of proliferating tumors/group) are compared using a Chi-squared test.

For tumor growth delay studies, drug treatment begins when the tumors reach 0.5 cm in diameter. The dose is set at half of the MTD, and the frequency of dosing is determined empirically in pilot studies, using up to daily doses for a maximum of 60 days.

The invention claimed is:

1. A method of treating a condition marked by abnormal cell growth which consists of treating breast cancer or endometrial cancer in a subject in need of treatment thereof, the method comprising administering to the subject a composition comprising a therapeutically effective amount of the compound

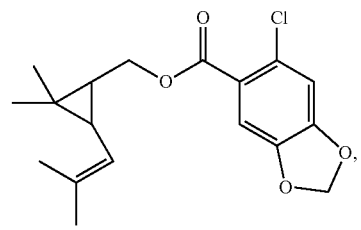 [SMILES: CC(C)=CC1C(COC(=O)c2cc3c(cc2Cl)OCO3)C1(C)C]

or a pharmaceutically acceptable salt thereof.

2. The method of claim 1, wherein the cells that are growing abnormally are estrogen-receptor positive (ER+) cells.

3. The method of claim 1, wherein the genome of the cells contains a BRCA1 mutation.

4. The method of claim 1, wherein the cells are resistant to tamoxifen or fulvestrant.

5. The method of claim 1, wherein the compound is co-administered with an agent selected from the group consisting of a *vinca* alkaloid, a nucleic acid inhibitor, a platinum agent, interleukin-2, an interferon, an alkylating agent, an antimetabolite, a corticosteroid, a DNA intercalating agent, an anthracycline and a urea.

6. The method of claim 1, wherein the compound is administered intravenously, intramuscularly, intraperitoneally or orally.

* * * * *

UNITED STATES PATENT AND TRADEMARK OFFICE
CERTIFICATE OF CORRECTION

PATENT NO. : 9,695,108 B2
APPLICATION NO. : 14/423290
DATED : July 4, 2017
INVENTOR(S) : Eliot M. Rosen, York A. Tomita and Milton Brown It is certified that error appears in the above-identified patent and that said Letters Patent is hereby corrected as shown below:

In the Specification

At Column 1, Lines 7-11, delete the following paragraph:
"Part of the work performed during development of this invention utilized U.S. Government funds under National Institutes of Health (National Cancer Institute) Grant Nos. R01-CA82599 and R01-CA150646. The U.S. Government has certain rights in this invention."

And insert in its place:
--This invention was made with government support under grant number CA82599 and CA150646 awarded by the National Institutes of Health. The government has certain rights in the invention.--

Signed and Sealed this
Twenty-second Day of October, 2024

Katherine Kelly Vidal
*Director of the United States Patent and Trademark Office*